US006825367B2

(12) United States Patent
Lalvani et al.

(10) Patent No.: US 6,825,367 B2
(45) Date of Patent: Nov. 30, 2004

(54) ELECTROCHEMICAL HYDROGENATION OF VEGETABLE OILS

(75) Inventors: Shashi B. Lalvani, Carbondale, IL (US); Kanchan Mondal, Carbondale, IL (US)

(73) Assignee: Board of Trustees of Southern Illinois University, Carbondale, IL (US)

( * ) Notice: Subject to any disclaimer, the term of this patent is extended or adjusted under 35 U.S.C. 154(b) by 55 days.

(21) Appl. No.: 10/395,006

(22) Filed: Mar. 21, 2003

(65) Prior Publication Data

US 2003/0213700 A1 Nov. 20, 2003

Related U.S. Application Data

(60) Provisional application No. 60/367,148, filed on Mar. 22, 2002.

(51) Int. Cl.[7] .................................... C07C 51/36

(52) U.S. Cl. .................... 554/147; 554/141; 554/124; 205/413; 205/462; 205/695; 205/696; 204/167

(58) Field of Search ............................ 554/147, 141; 205/413, 462, 695, 696; 204/167

(56) References Cited

U.S. PATENT DOCUMENTS 6,218,556 B1 * 4/2001 Pintauro .................... 554/124

* cited by examiner

*Primary Examiner*—Deborah D. Carr

(74) *Attorney, Agent, or Firm*—Harness, Dickey & Pierce, P.L.C.

(57) ABSTRACT

A method of electrochemically hydrogenating an oil, the method comprising reacting unsaturated fatty acids in the oil with hydrogen in the presence of a formate electrocatalyst.

20 Claims, 25 Drawing Sheets

ELECTROCHEMICAL HYDROGENATION OF VEGETABLE OILS

CROSS REFERENCE TO RELATED APPLICATION

This application claims priority to Provisional Patent Application Ser. No. 60/367,148, filed Mar. 22, 2002, incorporated herein in its entirety.

FIELD OF THE INVENTION

This invention relates to the electrochemical hydrogenation of fatty acids, and in particular of vegetable oils.

BACKGROUND OF THE INVENTION

Fatty acids are hydrogenated to improve their stability against oxidation, and improve their melting characteristics. Most current commercial hydrogenation processes are batch, rather than continuous processes, requiring high temperature and high-pressure reactors or vessels. These high temperature and high pressure processes suffer from a risk of explosion. Moreover because of the elevated temperature at which these processes operate, they result in the production of a higher percentage of trans fatty acids. Trans fatty acids are undesirable because they can increase the cholesterol levels in the blood, increase blood lipoprotein(s), and may be asscociated with the development and acceleration of coronary heart disease.

Another hydrogenation processes is catalytic transfer hydrogenation, for example as disclosed in Smidnovik et al., Smidnovik, A., Stimac, A., and Kobe, J., "Catalytic transfer hydrogenation of soybean oil", *JAOCS,* 69:405–409 (1992), incorporated herein by reference. Catalytic transfer hydrogenation requires substantial quantities of catalyst, which are consumed in the process, and thus the reaction rate also decreases over time. Still another hydrogenation process is electrocatalytic hydrogenation, for example as disclosed in Yusem, G. and Pintauro, P. N., "Electrochemical hydrogenation of soybean oil", *JAOCS,* 69, 399–404 (1992), Pintauro, U.S. Pat. No. 5,225,581, "Electrocatalytic process for hydrogenation of edible and non edible oils and fatty acids, the disclosures of both of which are incorporated herein by reference. Electrocatalytic hydrogenation typically results in the generation of $H_2$ which presents risk of explosion.

SUMMARY OF THE INVENTION

The present invention is a low temperature electrochemical hydrogenation process. The process results in substantial hydrogenation of fatty acids, but because it operates at relatively low temperatures, it results in relatively low production of trans fatty acids. Further the process regenerates the electrocatalyst, so that the reaction rate does not deleteriously decline over time.

There are other features and advantages will be in part apparent and in part pointed out hereinafter.

DETAILED DESCRIPTION OF THE INVENTION

This invention pertains to a method electrochemically hydrogenating an oil containing fatty acids. An oil usually contains a variety of fatty acids of varying degrees of saturation. For example, the primary constituents of soybean oil are Palmatic Acid (10%–12%) (16 carbon atoms; no double bonds); Stearic Acid (2.9%–4.1%) (18 carbon atoms; no double bonds); Oleic Acid (20%–22%) (18 carbon atoms; 1 double bond); Linoleic Acid (51%–53%) (18 carbon atoms; 2 double bonds); and Linolenic Acid (7%–9%)(18 carbon atoms; 3 double bonds). While soybean and canola oil are specifically discussed herein, the invention is not so limited and applies to any oil or combination of oils having unsaturated fatty acids. The process of hydrogenation adds 2 hydrogen atoms in place of a double bond in an unsaturated fatty acid. However in this process it is desirable to restrict the formation of undesirable trans-fatty acids, which are a common by-product of most hydrogenation processes, particularly those that operate at high temperatures.

Figure 1:
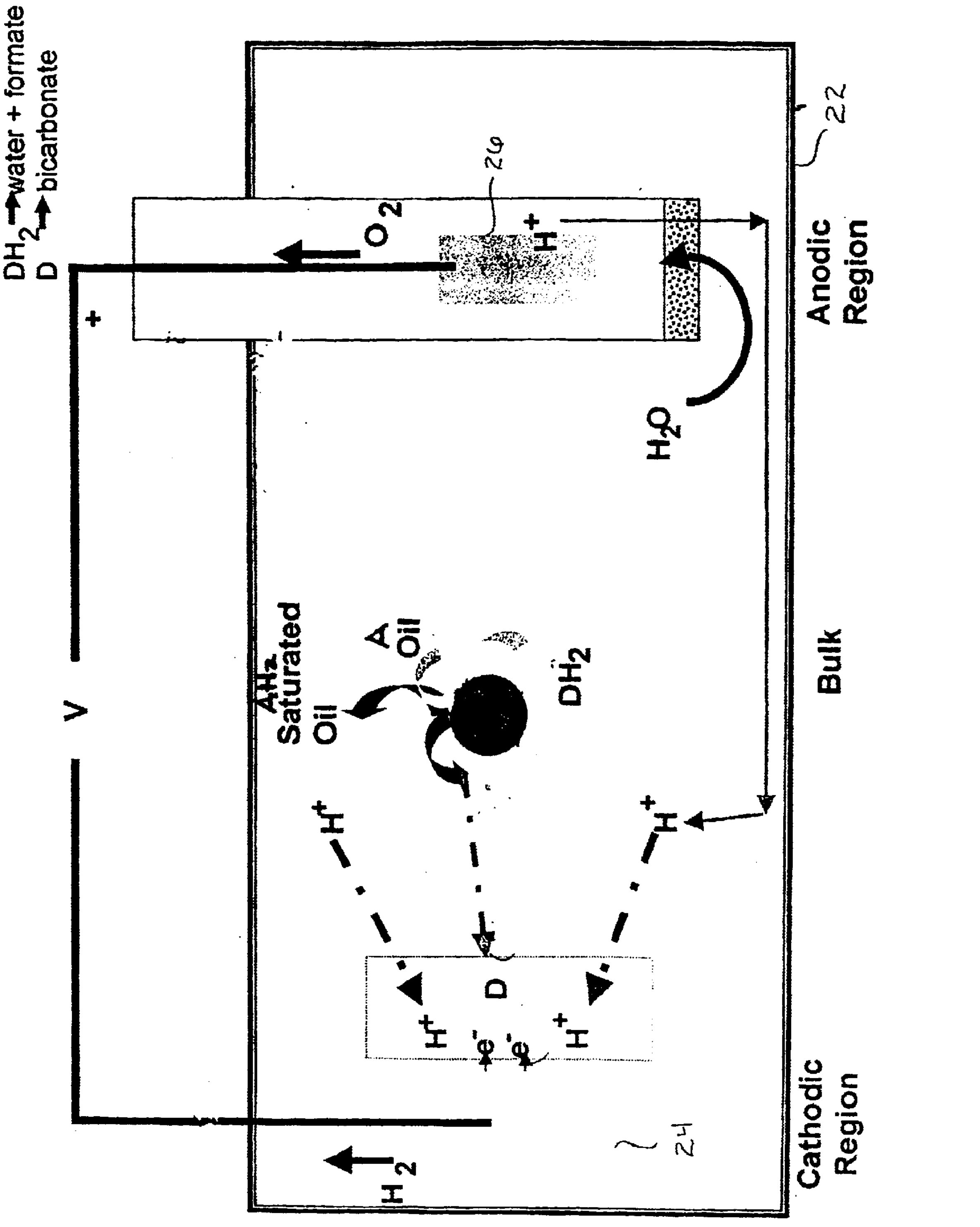
FIG. 1 is a schematic diagram of an electrocatalytic hydrogenation process according to the principles of this invention.

As shown in FIG. 1, a reaction chamber 22, containing a cathode, 24 which is filled with saturated oil while an electrolyte of desirable pH (usually an acid such as sulfuric acid) is placed in the anode, 26. Raney® nickel catalyst particles (available from W. R. Grace & Co.), and a regenerable catalyst, such as formic acid (HCOOH) formate salts and iron (III) triethanolamine. The reactions at the cathode are:

$$HCOO^-+A+H_2O \rightarrow AH_2+HCO_3^- \quad [1]$$

$$HCO_3^-+2H^++2e^- \rightarrow HCOO^-+H2O \quad [2]$$

$$2H^++2e^- \rightarrow H_2 \quad [3]$$

Where A represents the unsaturated oil.

The reactions at the anode are:

$$2H_2O \rightarrow 4H^++4e^-+O_2 \quad [4]$$

The overall reaction is:

$$A + 2H_2O \xrightarrow{HCOO^-} AH_2 + H_2 + O_2$$

As shown in FIG. 1, formic acid (HCOOH) and water, indicated as $DH_2$ in FIG. 1, react with oil A, producing a more saturated oil $AH_2$ and bicarbonate, indicated as D. At the cathode, the bicarbonate combines with $H^+$ ions and electrons to reform formic acid. Hydrogen gas, $H_2$, is also produced at the cathode 24. At the anode 26, water is broken down into $H^+$ ions and oxygen gas $O_2$. The result is that oil A combines with water $H_2O$ in the presence of the formic acid, and the oil becomes more saturated $AH_2$, and hydrogen $H_2$ is formed at the cathode 24, and oxygen $O_2$ is formed at the anode 26. Thus, the method of the invention provides catalytic transfer hydrogenation of fatty acids. The method generates hydrogen in situ using inexpensive materials. This hydrogen is used for hydrogenation of the oil and to replenish the hydrogen donor. Because the process can be conducted at low temperatures, the production of trans fatty acids is limited.

Figure 2:
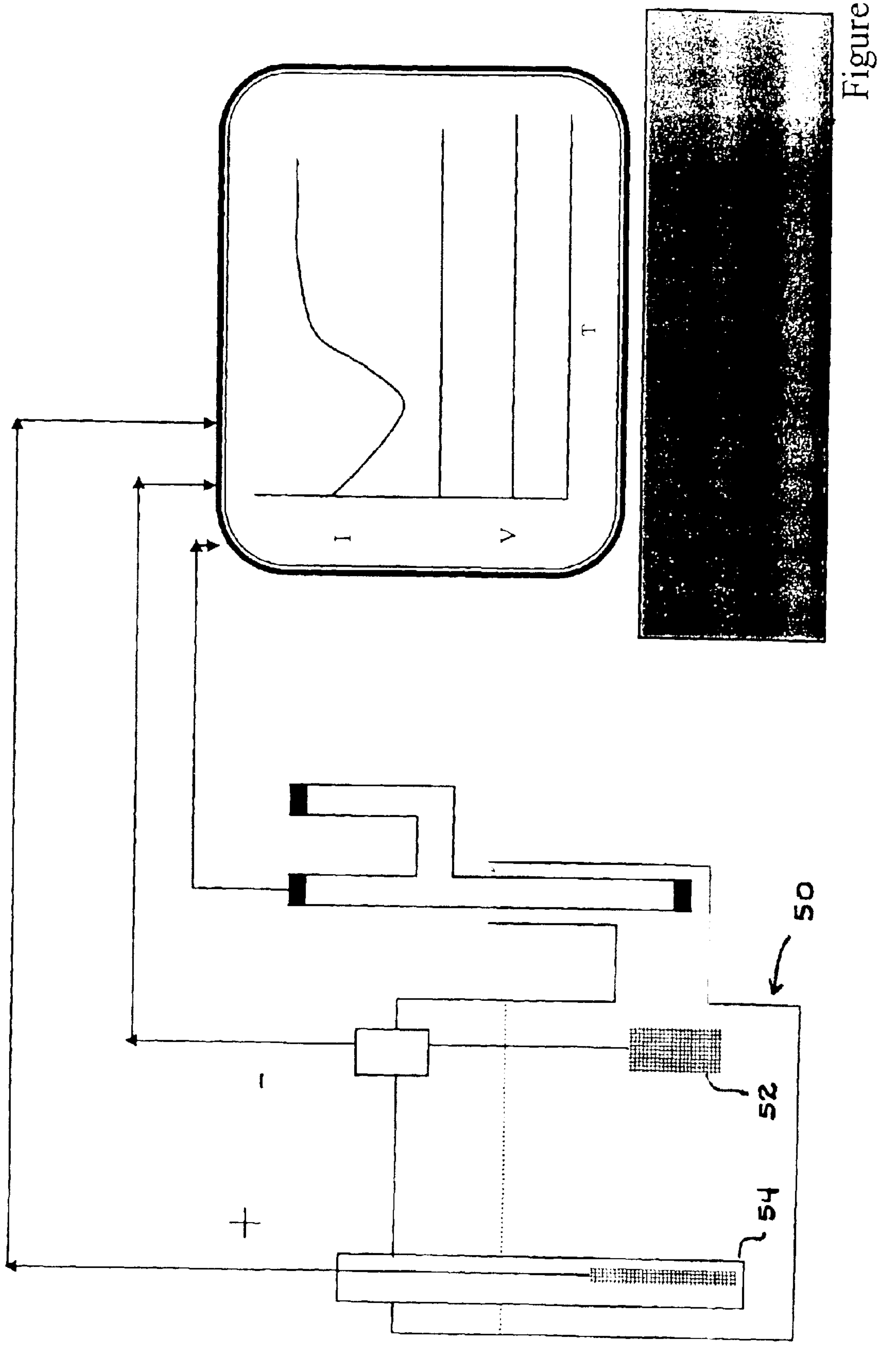
FIG. 2 is a schematic diagram of a laboratory set up for conducting an electrocatalytic hydrogenation process.

FIG. 2 is a schematic diagram of a laboratory set up for conducting an electrocatalytic hydrogenation process. As shown in FIG. 2 an electrochemical reactor 50 is divided into two major compartments, the cathode, 52 and anode, 54. The cathode 52 is filled with an emulsion of unsaturated oil and water while an electrolyte of desired pH is placed in the anode compartment 54. Electrocatalyst and catalyst are placed in the cathode compartment. A reference electrode 56 is provided to maintain a constant potential at the cathode 52. Current and potential versus time behavior of the process is maintained as represented by the graph on the right hand side of FIG. 2.

Figure 3:
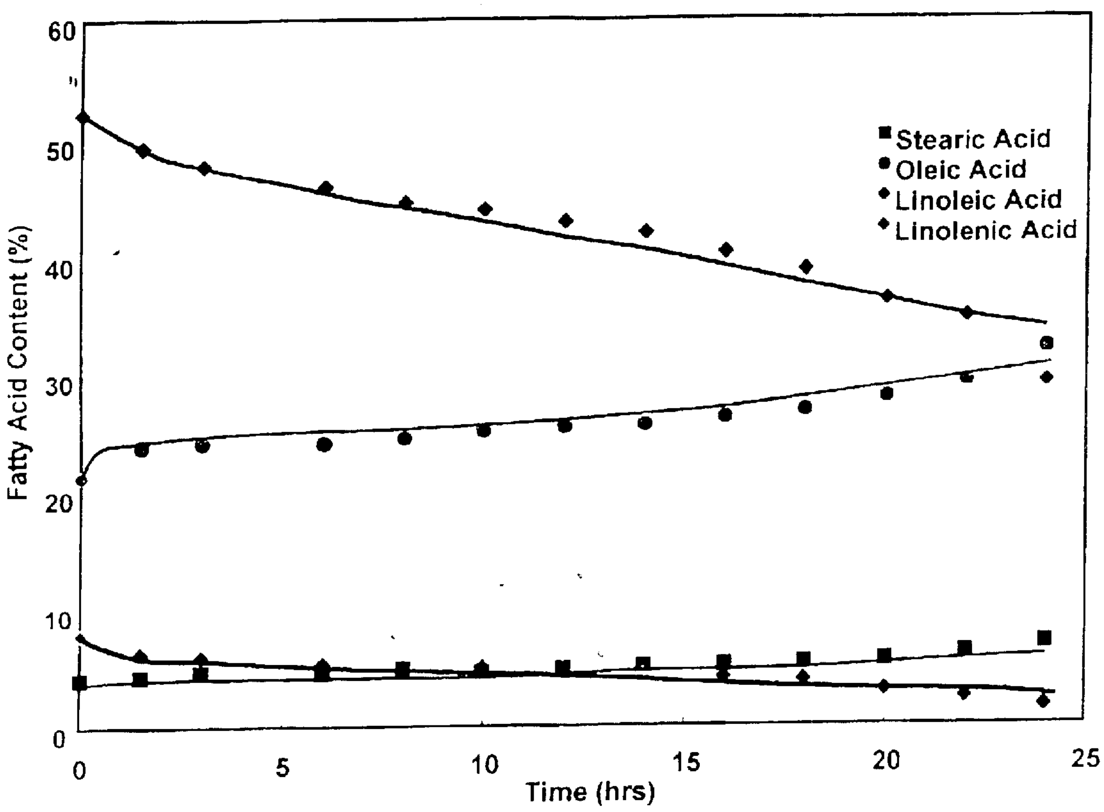
FIG. 3 is a graph showing the stearic, oleic, linoleic, and linolenic acid compositions versus time, with a hydrogenation process in accordance with the principles of this invention.

FIG. 3 is a graph showing the stearic, oleic, linoleic, and linolenic acid compositions versus time, with a hydrogenation process in accordance with this invention. This graph illustrates the reduction of linoleic ($C_{18}H_{32}O_2$) (18 carbon atoms: 2 double bonds) and linolenic ($C_{18}H_{30}O_2$) (18 carbon atoms: 3 double bonds) acids and the increase of the relatively more saturated oleic ($C_{18}H_{34}O_2$) (18 carbon atoms; 1 double bond) and stearic ($C_{18}H_{36}O_2$) (18 carbon atoms; 0 double bonds) acids.

Figure 4:
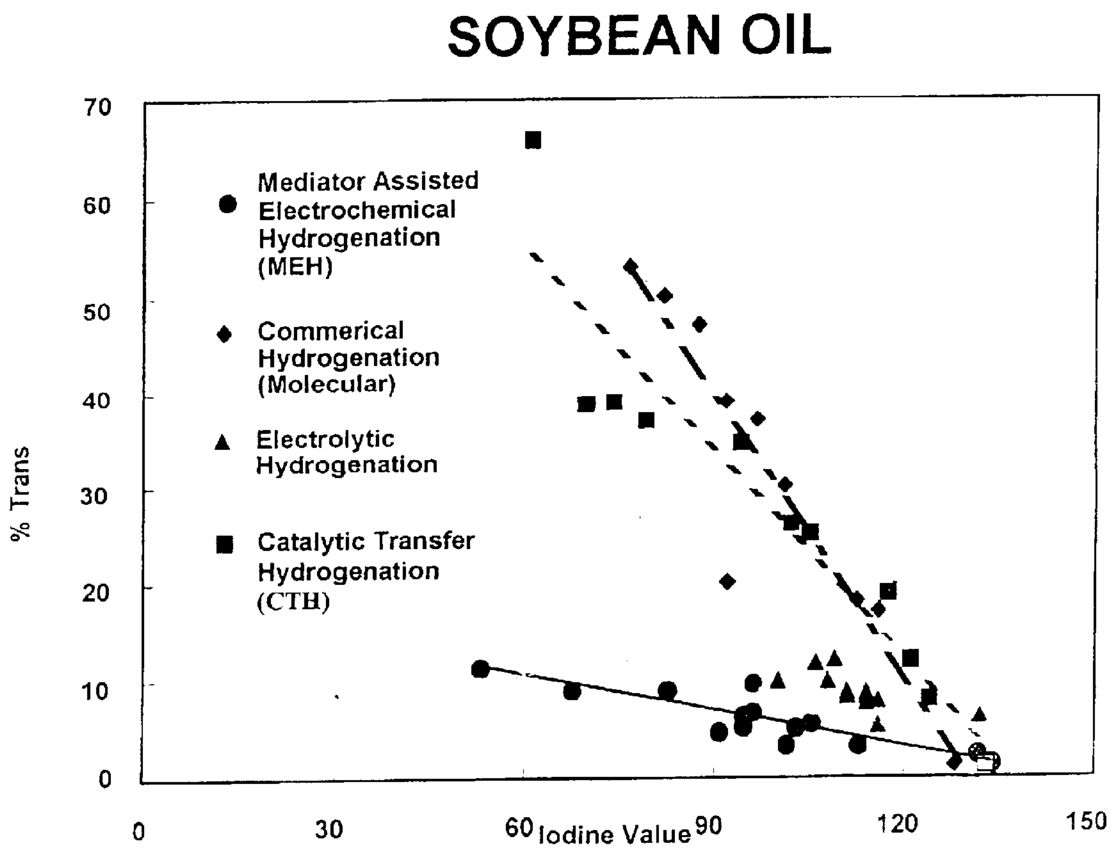
FIG. 4 is a graph of trans-fatty acid composition versus iodine value for mediator assisted electrochemical hydrogenation, commercial molecular hydrogenation, electrolytic hydrogenation, and catalytic transfer hydrogenation of soybean oil.

FIG. 4 is a graph of trans-fatty acid composition versus iodine value of soybean oil after mediator assisted electrochemical hydrogenation according to the principles of this invention, commercial molecular hydrogenation, electrolytic hydrogenation, and catalytic transfer hydrogenation. The FIG. 4 graph illustrates that as the iodine value of soybean oil subjected to the mediator assisted electrochemical hydrogenation of the present invention decreases (i.e. as the oil becomes increasingly saturated), the fraction of trans-fatty acids increases only modestly in comparison to other methods of hydrogenation, which are accompanied by much greater increases in the fraction of trans-fatty acids. This shows one of the benefits of hydrogenation using methods in accordance with the principles of the present invention over prior art methods of hydrogenation, and demonstrates the applicability of the method to soybean oil.

Figure 5:
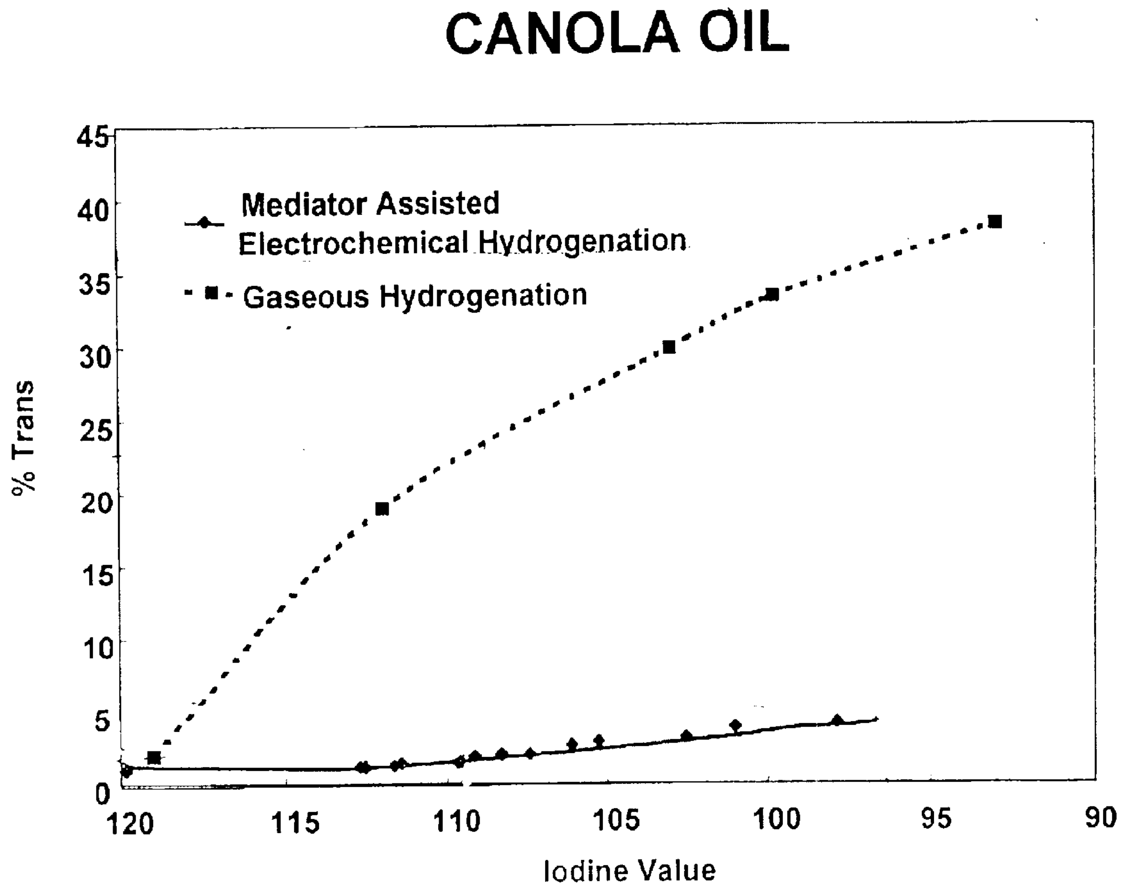
FIG. 5 is a graph of trans-fatty acid composition versus iodine value for mediator-assisted electrochemical hydrogenation and for gaseous hydrogenation of canola oil.

FIG. 5 is a graph of trans-fatty acid composition versus iodine value for canola oil for mediator assisted electrochemical hydrogenation according to the principles of the present invention and for gaseous hydrogenation. The graph illustrates that as the iodine value of canola oil subjected to the mediator assisted electrochemical hydrogenation in accordance with the principles of the present invention decreases (i.e. as the oil becomes increasingly saturated), the fraction of trans-fatty acids increases only modestly to a level of about 5%, in contrast to gaseous hydrogenation in which the fraction of trans-fatty acids increases to about 40%. This shows one of the benefits of hydrogenation using methods in accordance with the principles of the present invention over prior art methods of hydrogenation, and illustrates the applicability of the method to canola oil.

FIGS. 4 and 5 illustrate that the hydrogenation methods in accordance with the principles of this invention apply to fatty acids from any source, including vegetable oils and fats.

Figure 6:
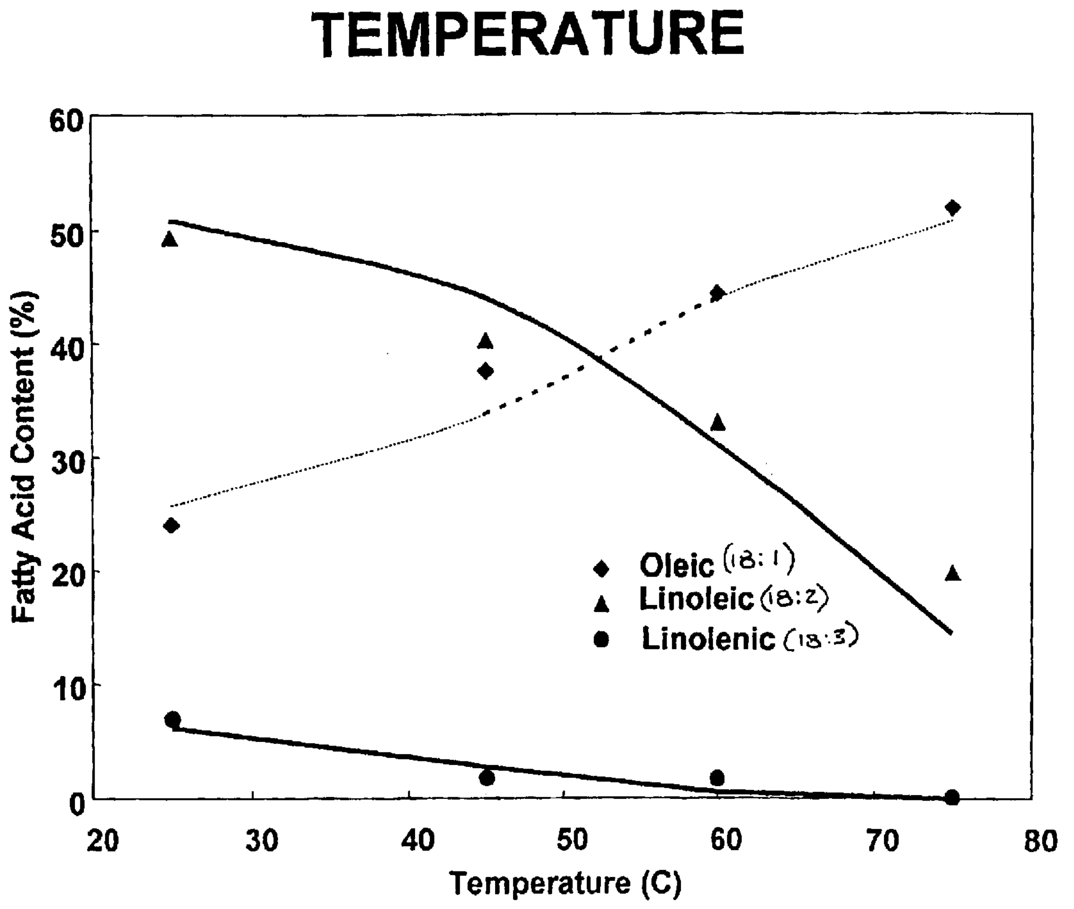
FIG. 6 is a graph of oleic, linoleic, and linoleneic acid content versus temperature for a hydrogenation process in accordance with this invention.

FIG. 6 is a graph of oleic, linoleic, and linolenic acid content versus temperature for a hydrogenation process in accordance with the principles of this invention. The FIG. 6 graph illustrates the effect of temperature on hydrogenation processes in accordance with the principles of this invention, showing that the fraction of the unsaturated fatty acids linolenic (18:3) and linoleic (18:2) decrease with increasing temperature, and the increase of the relatively more saturated oleic (18:1) increases with increasing temperature over the range of 30° C. to at least about 70° C., and particularly at temperatures above about 40°–45° C.

Figure 7:
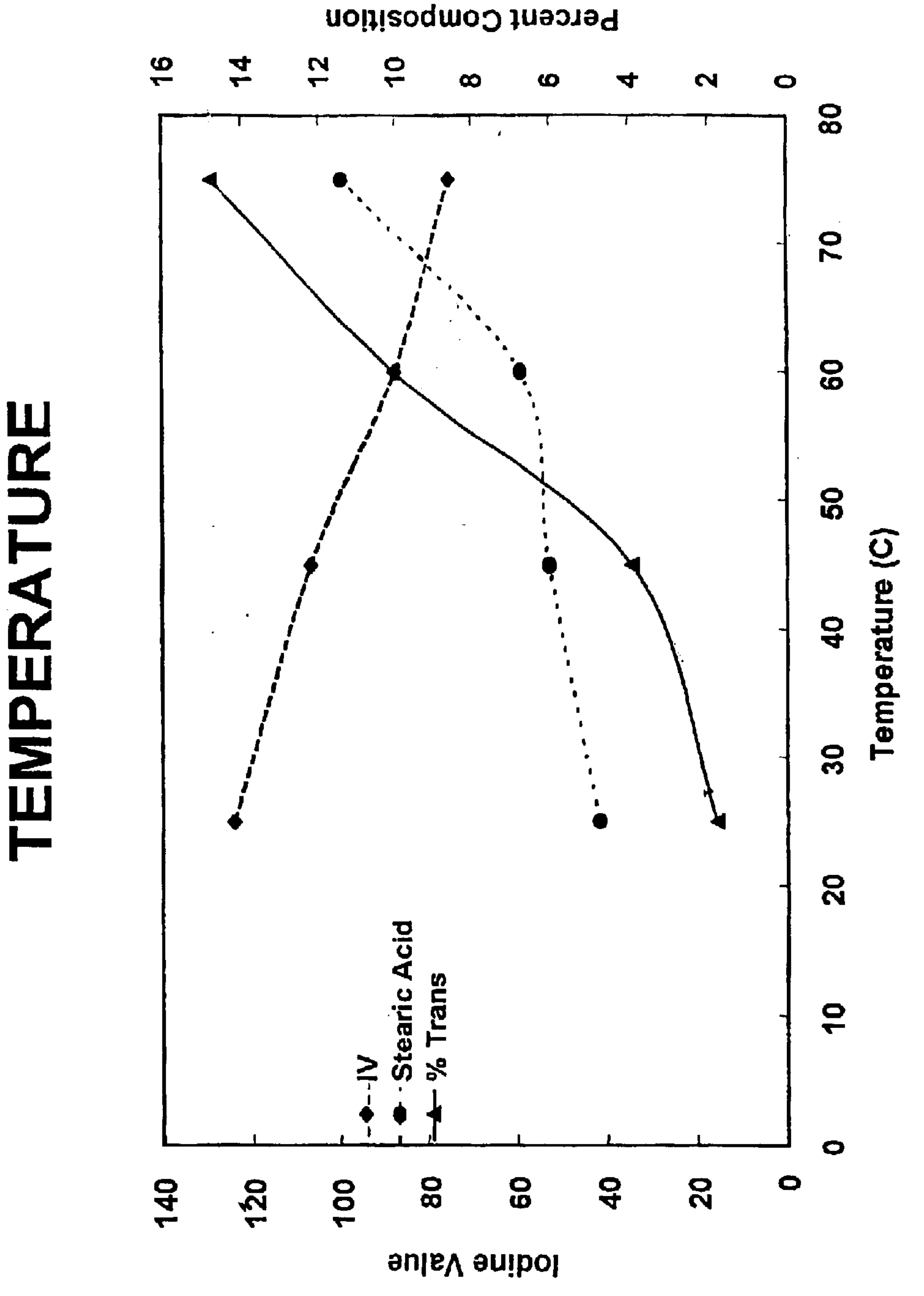
FIG. 7 is a graph of stearic acid and trans fatty acid composition (right side scale) and iodine value (left side scale) versus temperature for a hydrogenation process in accordance with the principles of this invention.

FIG. 7 is a graph of stearic acid and trans-fatty acid composition (right side scale) and iodine value (left side scale) versus temperature for a hydrogenation process in accordance with the principles of this invention. The FIG. 7 graph shows that as the temperature increases from about 25° C. to about 75° C., the iodine value (N) decreases steadily. The FIG. 7 graph also shows that as the temperature increases, the trans-fatty acid composition increases, at a moderate rate from about 25° C. to about 45° C., and at a steeper rate from about 45° C. to about 75° C. The FIG. 7 graph shows that as the temperature increases from about 25° C. to about 75° C., the saturated stearic (18:0) acid composition increases, at a moderate rate from about 25° C. to about 60° C., and at a steeper rate from about 60° C. to about 75° C.

Figure 8:
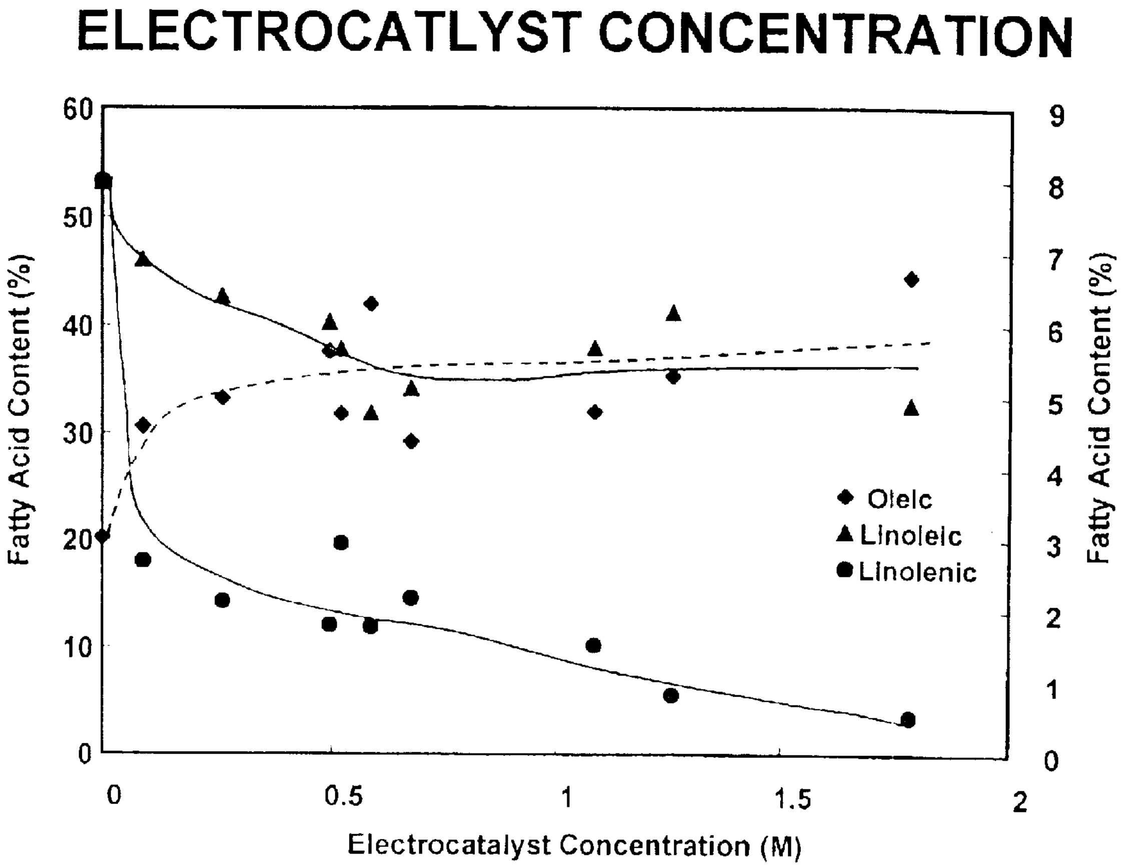
FIG. 8 is a graph showing oleic, linoleic, and linolenic composition versus electrocatalyst concentration for a hydrogenation process in accordance with this invention.

FIG. 8 is a graph showing oleic, linoleic, and linolenic composition versus electrocatalyst concentration for a hydrogenation process in accordance with the principles of this invention. The FIG. 8 graph shows that as electrocatalyst concentration (M) increases from about 0 to about 1.75 M, the linolenic (18:3) acid content decreases, rapidly as the electrocatalyst concentration increases from about 0 to about 0.2 M, and more slowly but steadily as the concentration increases from about 0.2 M to about 1.75 M. The FIG. 8 graphs also shows that as the electrocatalyst concentration increases from about 0 to about 0.5 M, the linoleic (18:2) acid content decreases, and as the electrocatalyst concentration increases from about 0.5 M to about 1.75 M, the linoleic acid content remains relatively constant. Finally, the FIG. 8 graph shows that the oleic acid content increases as the electrocatalyst concentration increases from about 0 to about 0.2 M, and remains relatively constant as the concentration increases from about 0.2 M to about 1.75 M.

Figure 9:
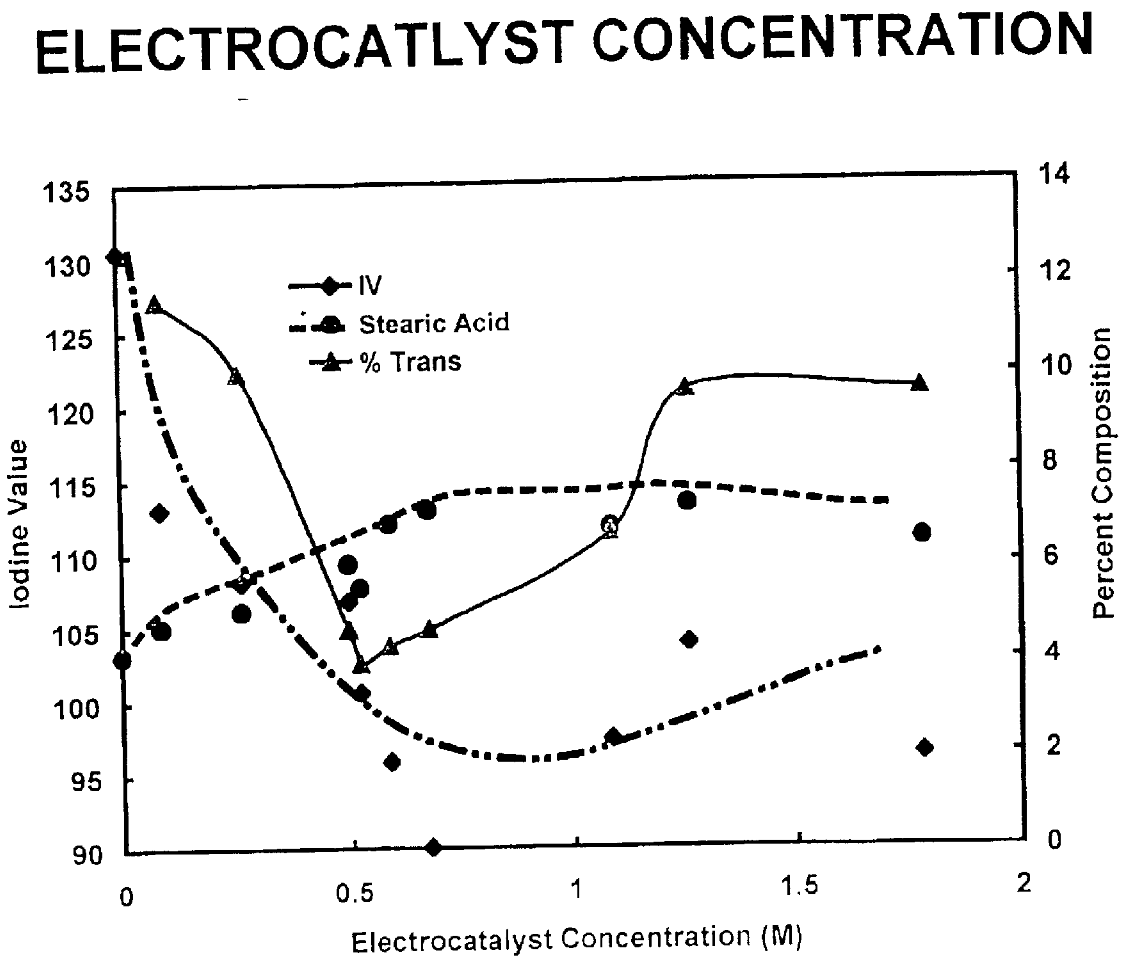
FIG. 9 is a graph of stearic acid and trans-fatty acid composition (right side scale) and iodine value (left side scale) versus electrocatalyst concentration for a hydrogenation process in accordance with the principles of this invention.

FIG. 9 is a graph of stearic acid and trans-fatty acid composition (right side scale) and iodine value (left side scale) versus electrocatalyst concentration for a hydrogenation process in accordance with the principles of this invention. The FIG. 9 graph shows that in the preferred embodiment, the iodine value decreases with increasing electrocatalyst composition from 0 to about 0.75 M, and at concentrations above about 0.75 M begins to increase. The FIG. 9 graph also shows that the fraction of trans-fatty acid decreases with increasing electrocatalyst composition from 0 to about 0.5 M, and the fraction of trans-fatty acids begins to increase as the electrocatalyst concentration increases from about 0.5 M, and increases more sharply as the electrocatalyst concentration increases from about 1.0 M. Finally, the FIG. 9 graph shows that the stearic acid content increases slightly as electrocatalyst concentration increases from about 0 to about 0.5–0.7 M, and remains substantially constant at concentrations above about 0.5–0.7 M.

Figure 10:
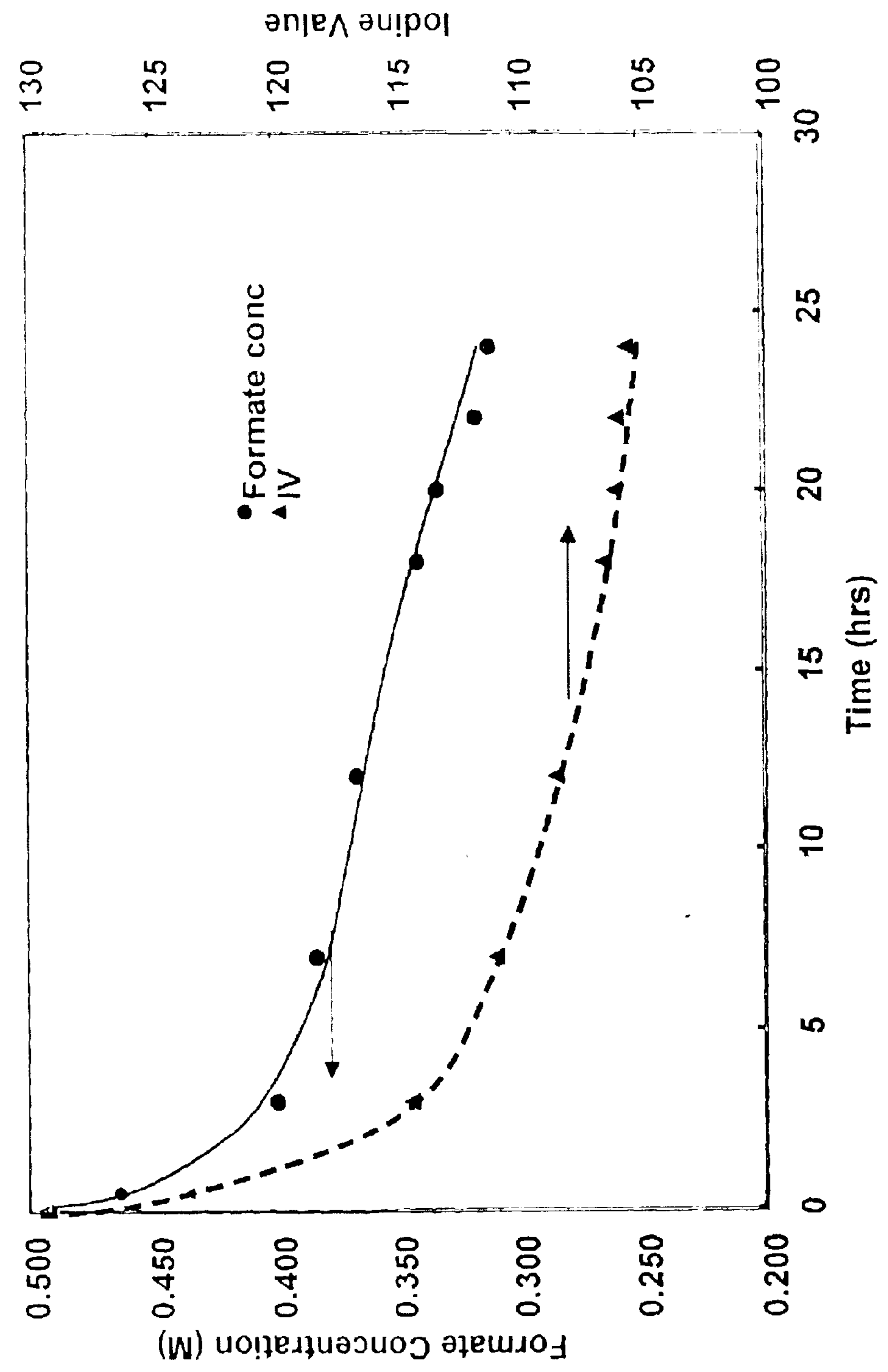
FIG. 10 is a graph of formate concentration (left side scale) and iodine value (right side scale) versus time for a hydrogenation process in accordance with this invention.

FIG. 10 is a graph of formate concentration (left side scale) and iodine value (right side scale) versus time for a hydrogenation process in accordance with the principles of this invention. The FIG. 10 graph shows that formate concentration decreases sharply for up to about 3 hours, and thereafter decreases more slowly. This confirms that the method of this invention regenerates the formate ion catalyst. The FIG. 10 graph also shows that iodine value decreases sharply for up to about 3 hours, and decreases more slowly. This illustrates that methods in accordance with the principles of this invention continue to hydrogenate fatty acids (indicated by the decreasing iodine value) over extended period of time, even as the formic acid is regenerated.

Figure 11:
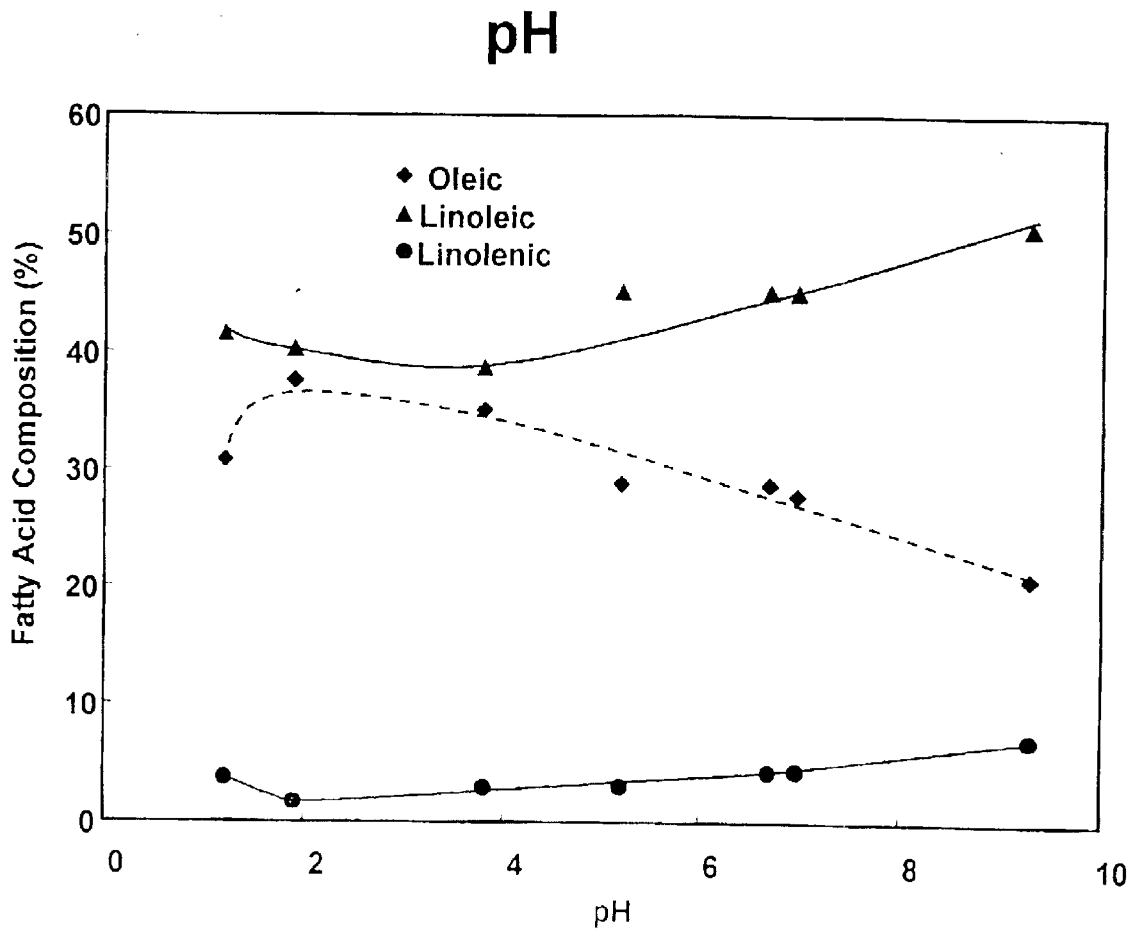
FIG. 11 is a graph of oleic, linoleic, and linolenic acid content versus pH for a hydrogenation process in accordance with the principles of this invention.

FIG. 11 is a graph of oleic, linoleic, and linolenic acid content versus pH for a hydrogenation process in accordance with the principles of this invention. The FIG. 11 graph shows that for pH from about 1 to about 4 the fraction of linoleic acid appears to decrease slightly. Thereafter, from a pH of about 4 to at least about 9, the fraction of linoleic acid increases from about 40% to as much as about 50%. As also shown in FIG. 11, the fraction of oleic acid appears to increase slightly as the pH increases from about 1 to about 2. Thereafter, from a pH of about 2 to a pH of at least about 9, the fraction of oleic acid decreases from about 40% to about 20%. Finally, the FIG. 11 graph shows that for pH from about 1 to about 2 the fraction of linolenic acid appears to decrease slightly. Thereafter, from a pH of about 2 to at least about 9, the fraction of linolenic acid increases from about 2% to as much as 10%.

Figure 12:
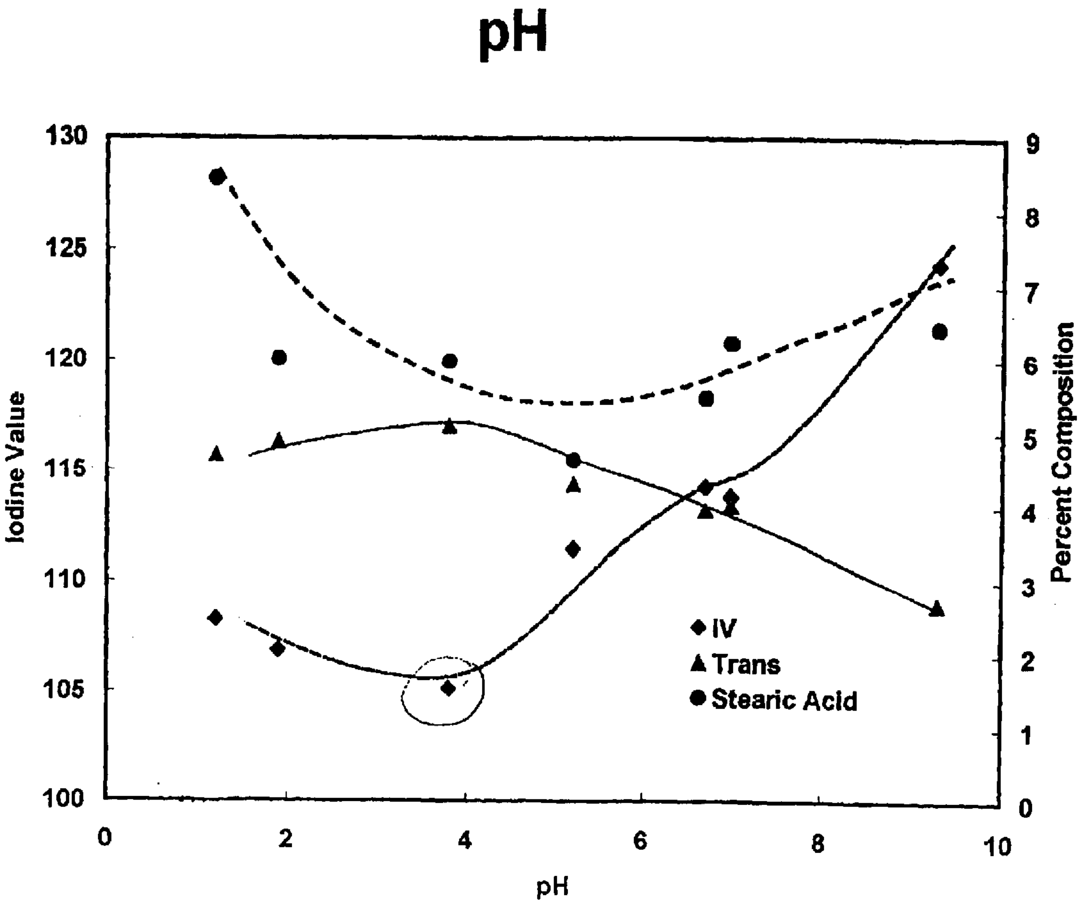
FIG. 12 is a graph of stearic and trans-fatty acid content (right side scale) and iodine value (left hand scale) versus pH for a hydrogenation process in accordance with the principles of this invention.

FIG. 12 is a graph of stearic and trans-fatty acid content (right side scale) and iodine value (left hand scale) versus pH for a hydrogenation process in accordance with the principles of this invention. The FIG. 12 graph shows that the fraction of stearic acid decreases from a pH of about 1 to about 4, and thereafter increases from a pH of about 4 to a pH of at least about 9 from about 6 percent to about 7 percent. The FIG. 12 graph also shows that the fraction of trans-fatty acids increases slightly from a pH of about 1 to a pH of about 4, and decreases from 5 percent to about 2.5 percent as the pH increases a pH of about 4 to a pH of about 0. Finally, the FIG. 12 graph shows that the iodine value decreases from about 108 to about 105 as the pH increases from about 1 to about 4. Thereafter, the iodine value increases as the pH increases from about 4 to at least about 9.

Figure 13:
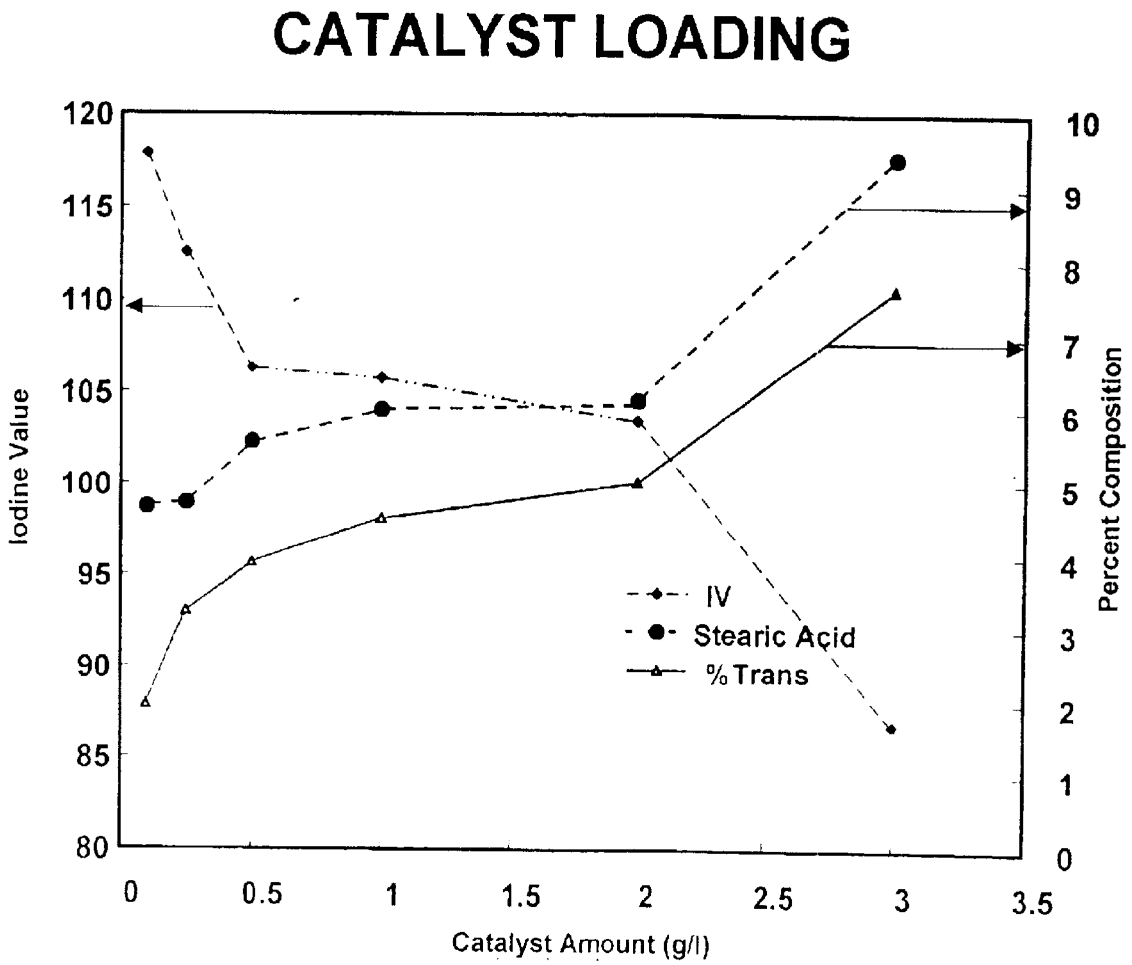
FIG. 13 is a graph of stearic acid and trans-fatty composition (right side scale) and iodine value (left side scale) versus catalyst amount for the hydrogenation process in accordance with the principles of this invention.

FIG. 13 is a graph of stearic acid and trans-fatty acid composition (right side scale) and iodine value (left side scale) versus catalyst amount for hydrogenation process in accordance with the principles of this invention. The FIG. 13 graph shows that the fraction of stearic acid increases slightly as catalyst concentration increases from 0 g/l to about 2 g/l, and increases sharply as catalyst concentration increases from about 2 g/l. The FIG. 13 graph also shows that the fraction of trans-fatty acids increases slightly as catalyst concentration increases from 0 g/l to about 2 g/l, and increases sharply as catalyst concentration increases from 2 g/l. However trans-fatty acid concentration still remains less than about 10 percent, and below 8 percent for concentrations up to about 3 g/l. Finally, the FIG. 13 graph shows that the iodine value decreases sharply as catalyst concentration increases from 0 to about 0.5 g/l, decreases slightly as catalyst concentration increases from about 0.5 g/l to 2 g/l, and again decreases sharply as catalyst concentration increases from about 2 g/l. The FIG. 13 graph shows that the method of the present invention is particularly effective at catalyst concentrations above about 2 g/l.

Figure 14:
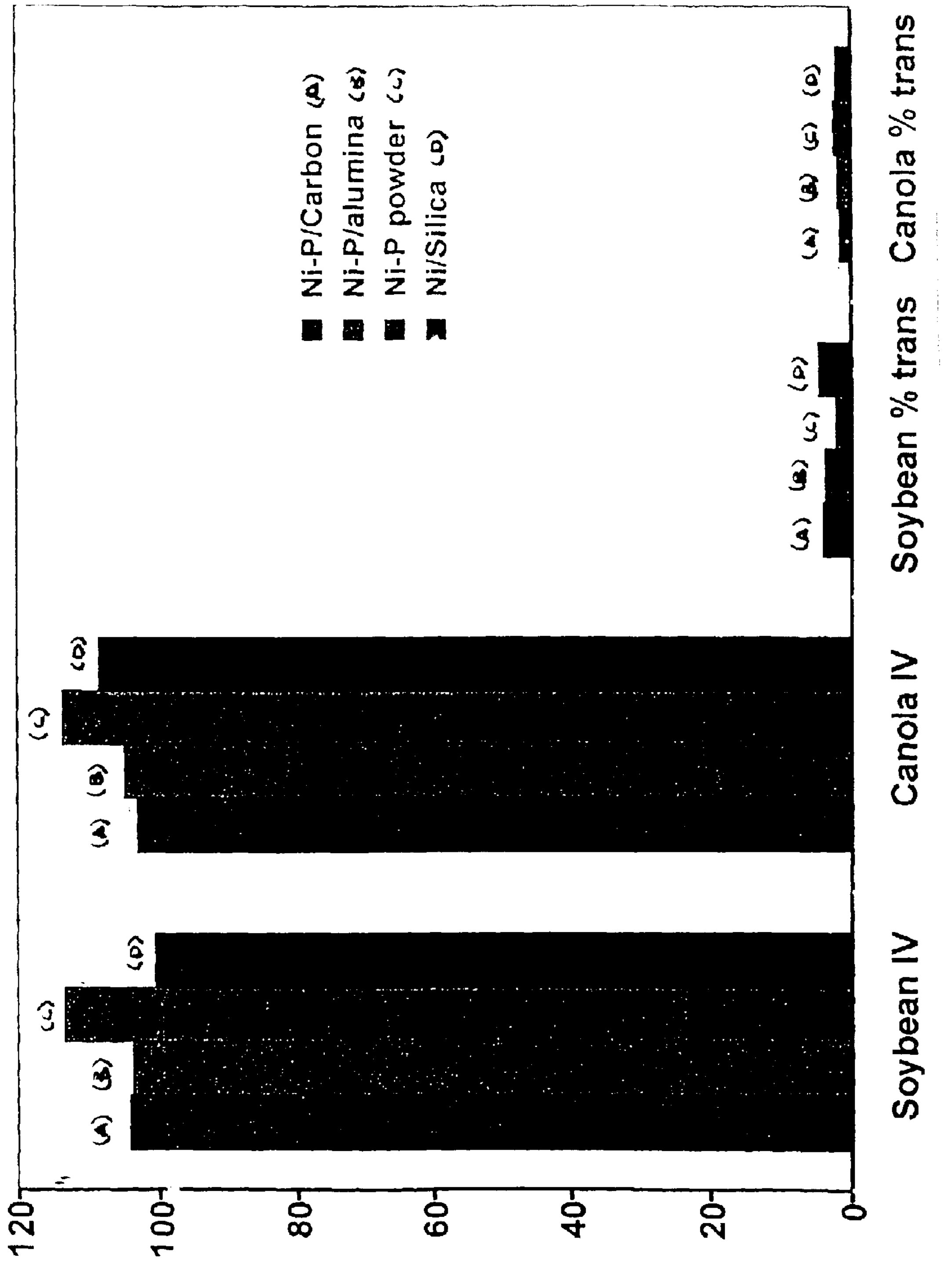
FIG. 14 is a bar graph showing the relative performance of various catalysts in reducing the iodine value of soybean oil and canola oil for a hydrogenation process in accordance with the principles of this invention, and showing the relative formation of trans-fatty acids with those same catalysts for soybean oil and canola oil for a hydrogenation process in accordance with the principles of this invention.

FIG. 14 is a bar graph showing the relative performance of various catalysts in reducing the iodine value (IV) of soybean oil and canola oil for a hydrogenation process in accordance with the principles of this invention, and showing the relative formation of trans-fatty acids with those same catalysts for soybean oil and canola oil for a hydrogenation process in accordance with the principles of this invention. The FIG. 14 graph shows that the performance of Ni—P/Carbon, Ni—P/alumina, the Ni—P powder, and Ni/Silica all perform relatively similarly, achieving iodine values of about 100 for both soybean oil and canola oil, with the Ni/Silica performing the best for soybean oil, and the Ni—P/Carbon performing the best for canola oil. The FIG. 14 graph also shows that the formation of trans fatty acids for both soybean oil and canola oil is relatively low, with total trans-fatty acid content less than 5%. The trans-fatty acid content of the canola oil is slightly lower than for soybean oil, but the trans-fatty acid content is still significantly less than with other hydrogenation processes.

Generally, the nickel content in the hydrogenated oil 0–1.4 ppm. However, in the specific case of the comparison at 3.8: pH Ni/silica–commercial=8.1 ppm; NiP powder (amorphous nickel)=13.16 ppm; NiP/carbon (amorphous nickel)=4.21 ppm; NiP/alumina (amorphous nickel)=1.17 ppm.

Figure 14A:
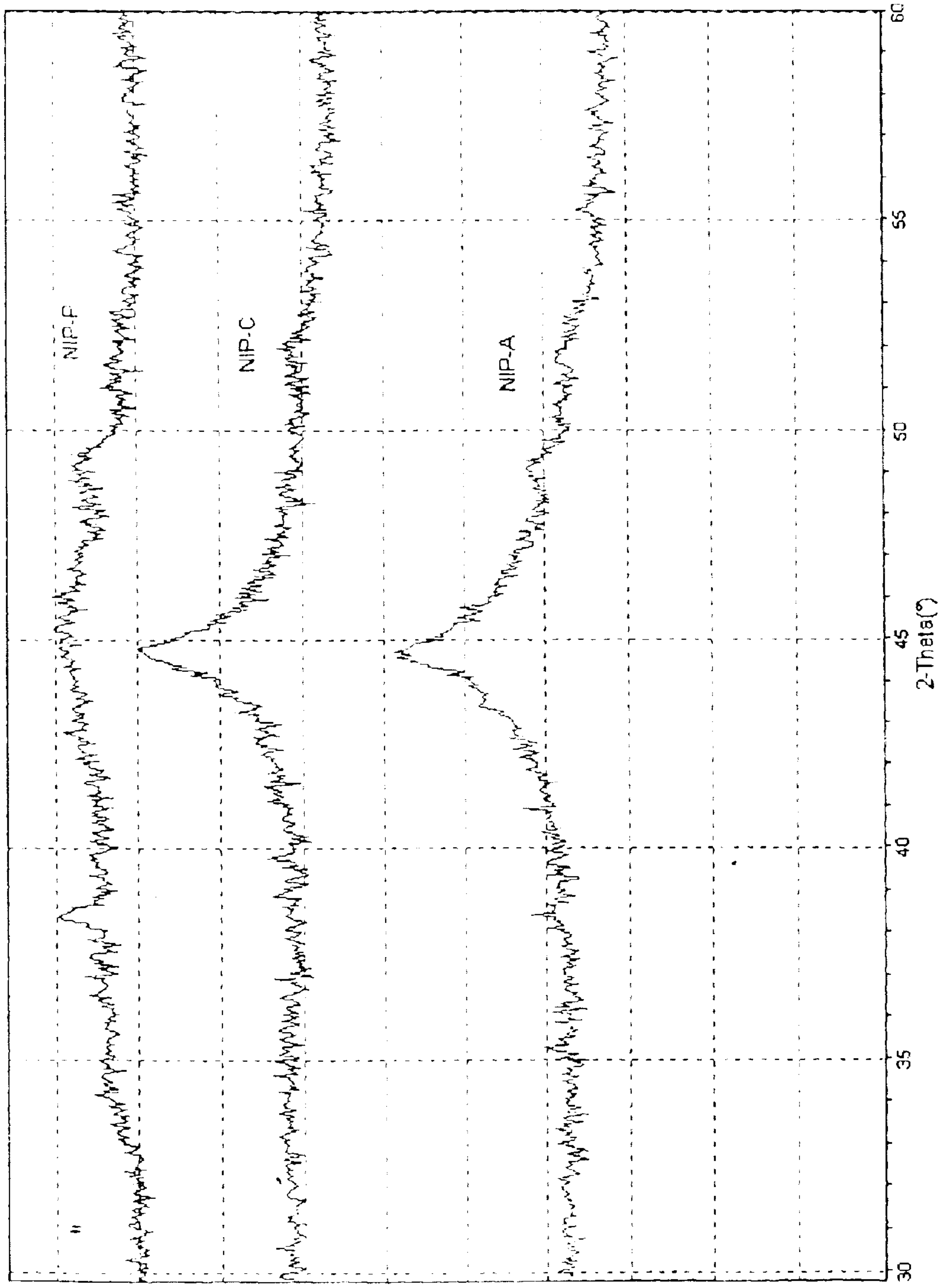
FIG. 14A is an x-ray diffraction spectra for the Ni—P/Carbon (NIP—C), Ni—P/powder (NIP—P), and the Ni—P/alumina (NIP—A) catalysts useful in hydrogenation processes in accordance with the principles of this invention.

FIG. 14A is an x-ray diffraction spectra for the Ni—P/Carbon, Ni—P/powder, and the Ni—P/alumina catalysts which shows that the catalysts are amorphous.

Figure 15:
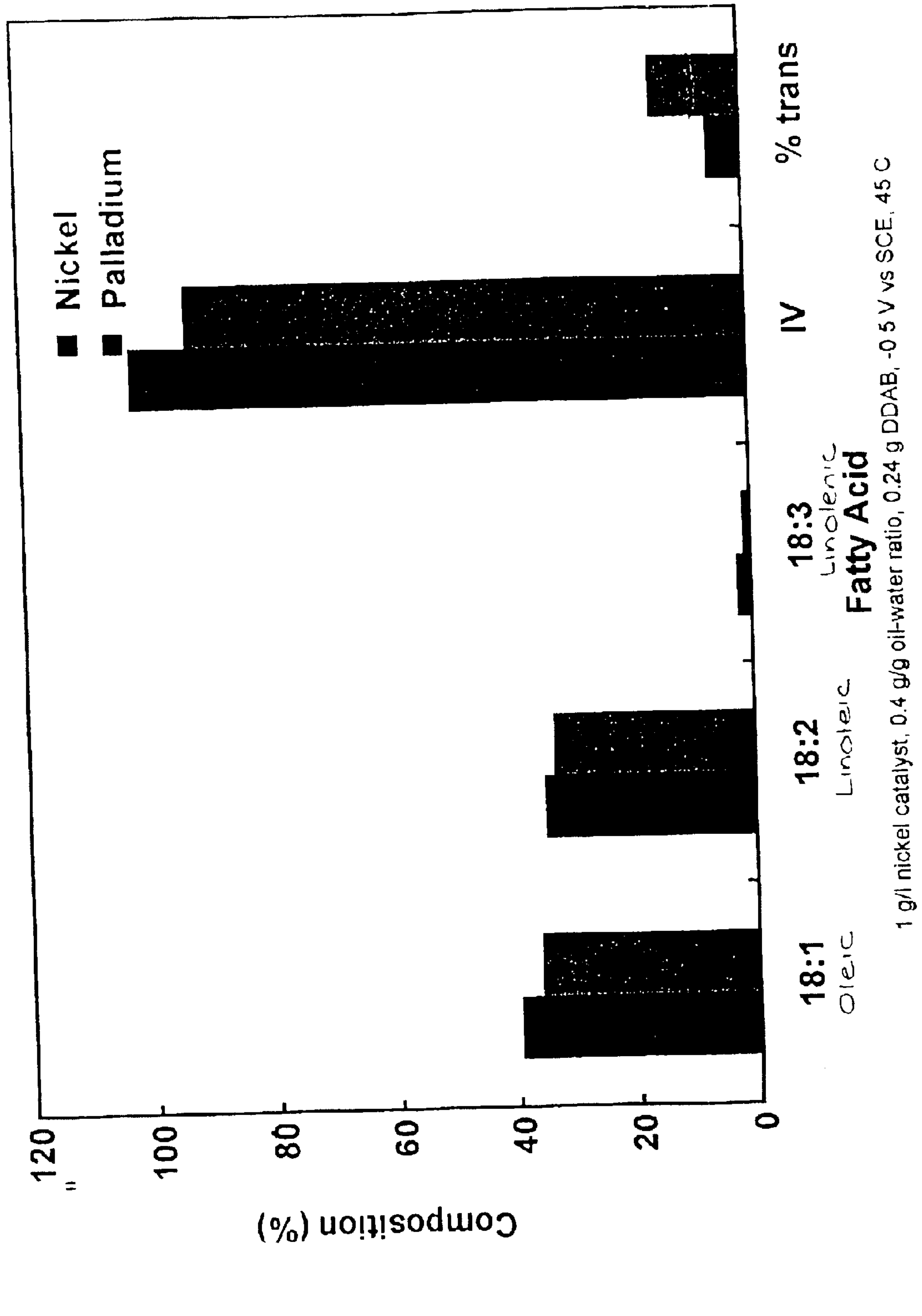
FIG. 15 is a bar graph of compositions of oleic, linoleic, and linolenic and trans-fatty acids; and the iodine value using nickel and palladium catalysts in a hydrogenation process in accordance with the principles of this invention.

FIG. 15 is a bar graph of the compositions of oleic, linoleic, and linolenic and trans-fatty acids; and the iodine value for nickel and palladium catalysts for a hydrogenation process of this invention. The FIG. 15 graph shows that the concentration of oleic (18:1) acid for both catalysts is about the same—about 40%; the composition of the more unsaturated linoleic (18:2) acid for both catalysts is about the same—under 40%; the composition of the more unsaturated linolenic (18:3) acid for both catalysts is about the same—under 2%.

Figure 16:
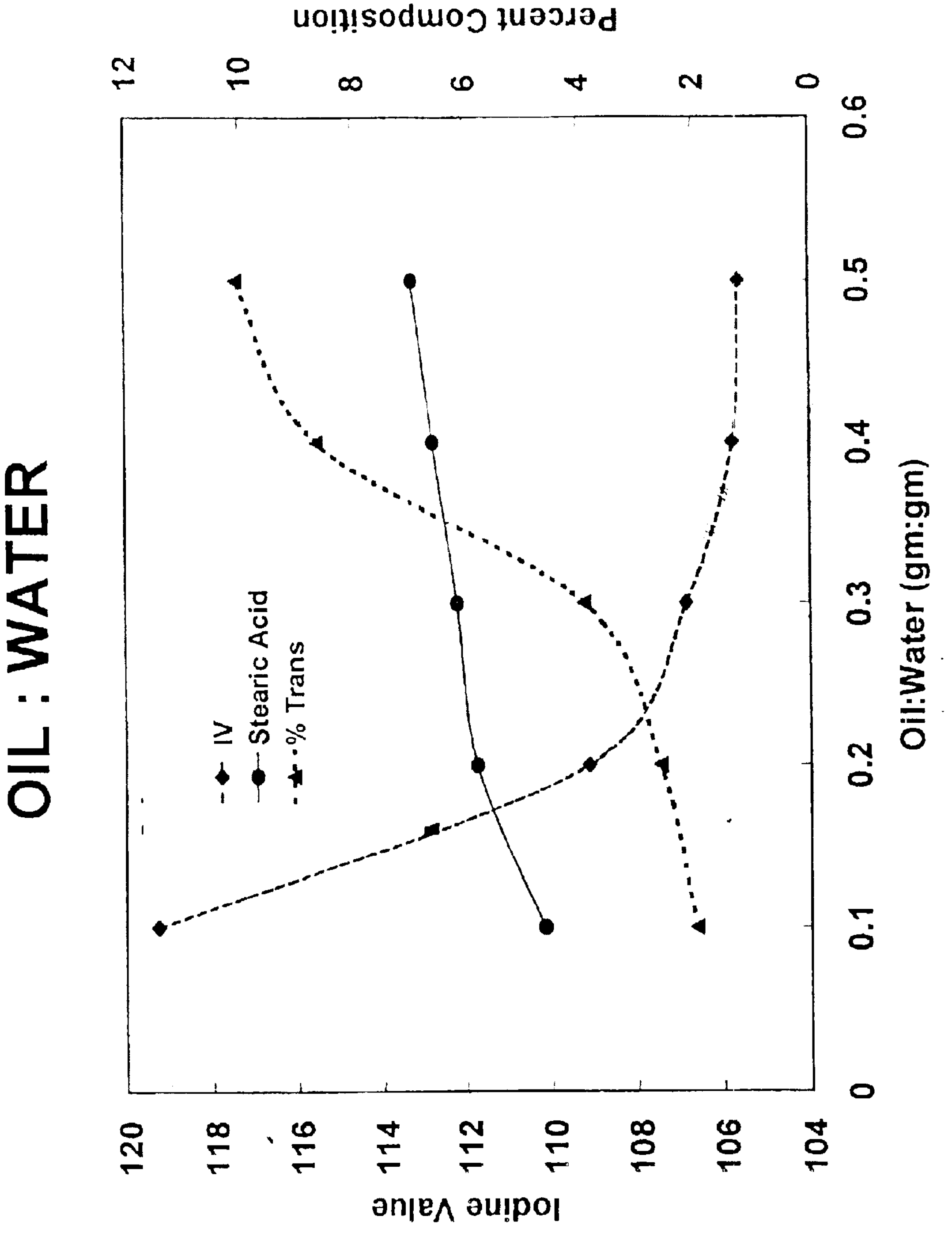
FIG. 16 is a graph of stearic and trans-fatty acid composition (right side scale) and iodine value (left side scale) verses oil:water ratio for a hydrogenation process in accordance with the principles of this invention.

FIG. 16 is a graph of stearic and trans-fatty acid composition (right side scale) and iodine value (left side scale) versus oil:water ratio for a hydrogenation process in accordance with the principles of this invention. The FIG. 16 graph shows that the stearic acid content increases as the oil:water ratio increases from about 0.1 to about 0.5. The FIG. 16 graph also shows that trans-fatty acid content increases as the oil:water ratio increases, and particularly at oil:water ratios above about 0.3. Finally, the FIG. 16 graph shows that the iodine value decreases sharply as the oil:water ratio increases from about 0.1 to about 0.3, but the iodine value continues to decrease, although at a lesser rate, as the oil:water ratio increases from 0.3 to about 0.5.

Figure 17:
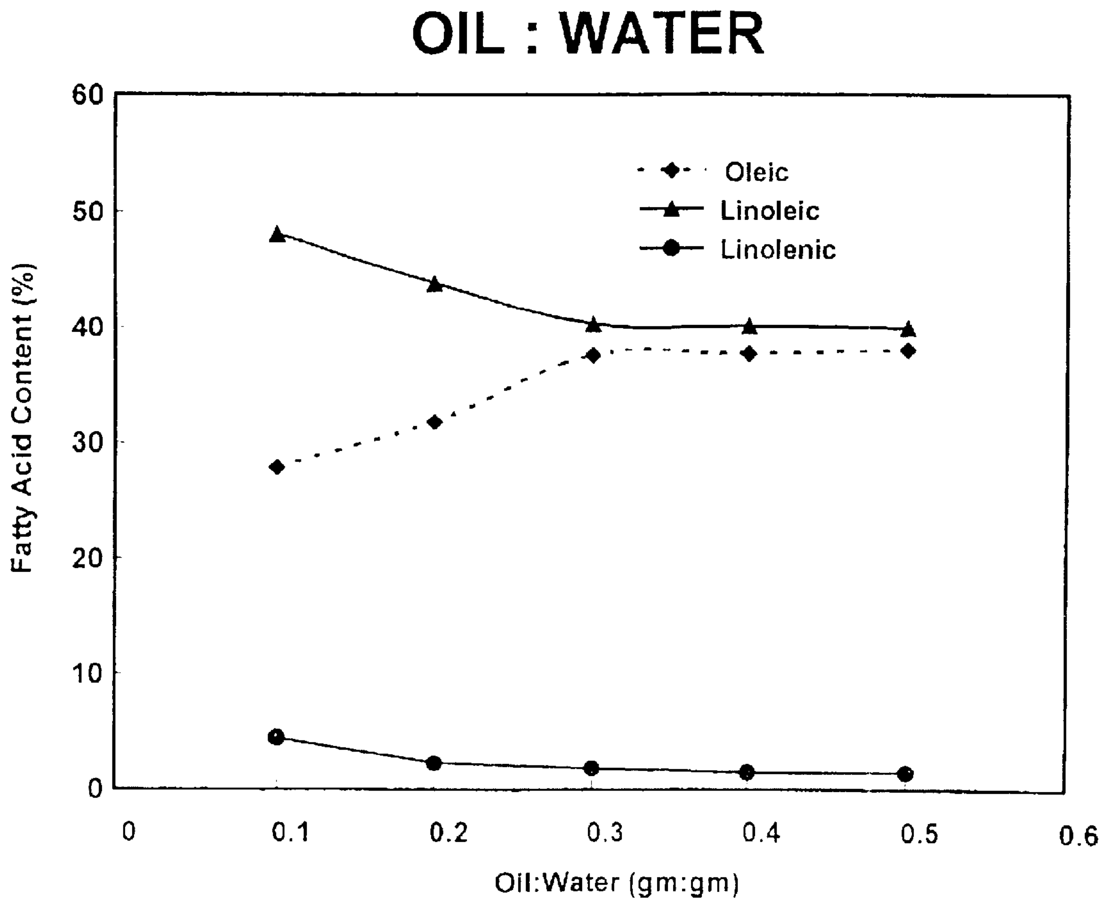
FIG. 17 is a graph of oleic, linoleic, and linolenic acid content versus oil:water ratio for a hydrogenation process of this invention.

FIG. 17 is a graph of oleic, linoleic, and linolenic acid content verses oil:water ratio for a hydrogenation process in accordance with the principles of this invention. The FIG. 17 graph shows that the concentration of linoleic (18:2) acid and linolenic (18:3) acid decreases as the oil:water ratio increases from about 0.1 to about 0.3, but remains relatively constant at oil:water ratios above about 0.3. The FIG. 17 graph also shows that the relatively more saturated oleic acid (18:1) concentration increases as the oil:water ratio increases from about 0.1 to about 0.3, but remains relatively constant at oil:water ratios above about 0.3.

Figure 18:
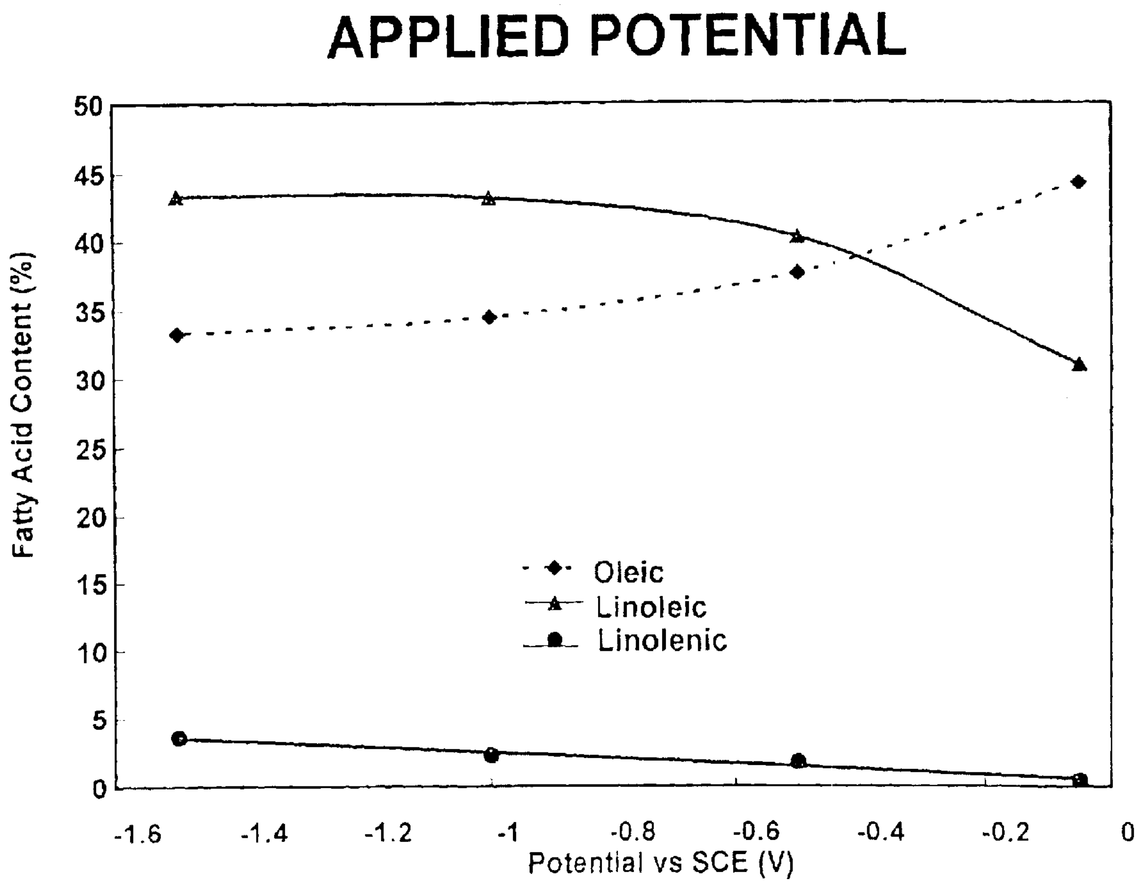
FIG. 18 is a graph of oleic, linoleic, and linolenic acid compositions versus applied potential for a hydrogenation process in accordance with the principles of the present invention.

FIG. 18 is a graph of oleic, linoleic, and linolenic acid compositions versus applied potential for a hydrogenation process in accordance with the principles of the present invention. The FIG. 18 graph shows that as the potential difference decreases from about −1.5 V to about −0.05 V, the content of linolenic (18:3) acid decreases relatively steadily. The FIG. 18 graph also shows that as the potential difference decreases from about −1.5 V to about −0.05 V the linoleic (18:2) acid content decreases, and particularly as the potential difference decreases from about −0.5 V to about −0.05 V the linoleic acid content decreases. Finally, the FIG. 18 graph shows that as the potential difference decreases from about −1.5 V to about −0.05 V the relatively more saturated oleic (18:1) acid content increases, and particularly as the potential difference decreases from about −0.5 V to about −0.05 V, the oleic acid content increases.

Figure 19:
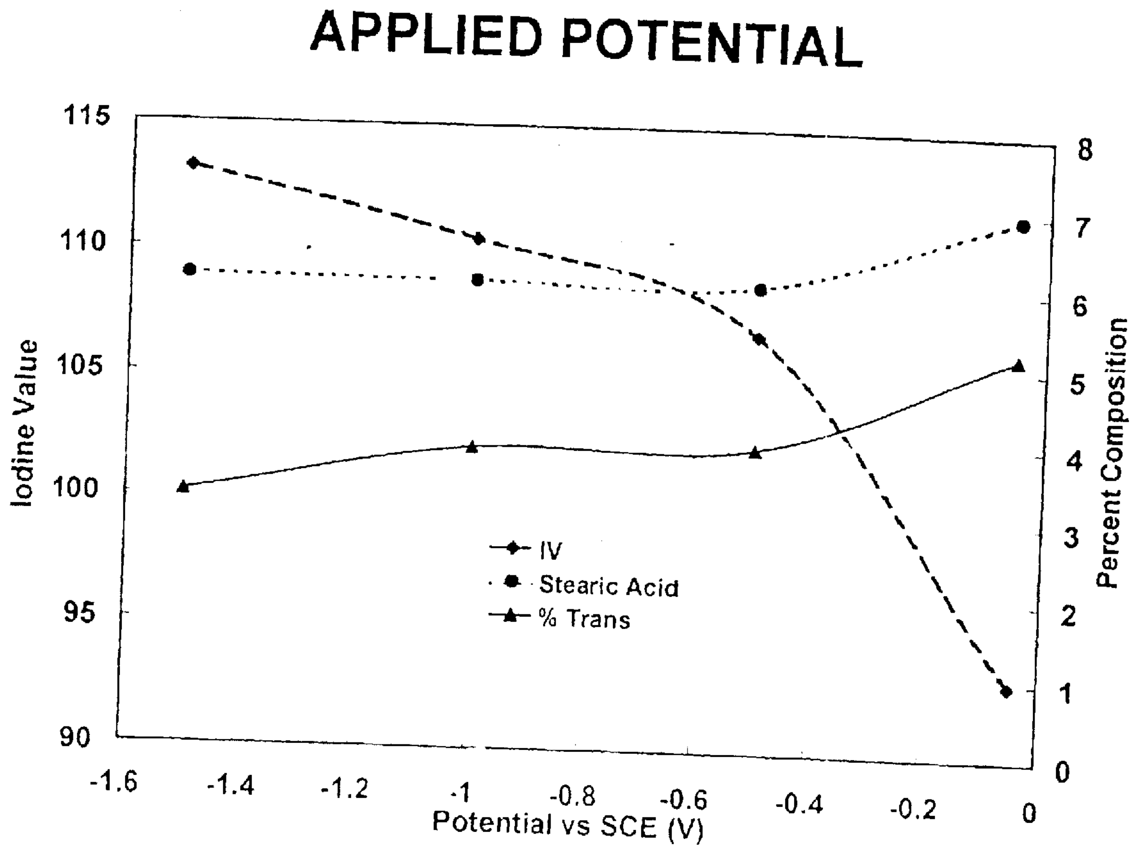
FIG. 19 is a graph showing stearic and trans-fatty acid composition (right side scale) and iodine value (left side scale) versus applied potential for a hydrogenation process in accordance with the principles of this invention.

FIG. 19 is a graph showing stearic acid and trans-fatty acid composition (right side scale) and iodine value (left side scale) versus applied potential for a hydrogenation process in accordance with the principles of this invention. The FIG. 19 graph shows that as the potential difference decreases from about −1.5 V to about −0.05 V, the content of saturated stearic (18:0) acid increases relatively steadily, increasing slightly more rapidly as the potential difference decreases from −0.5 V to about −0.05 V. The FIG. 19 graph also shows that as the potential difference decreases from about −1.5 V to about −0.05 V the trans-fatty acid composition increases slightly, increasing more sharp as the potential difference decreases from about −0.5 V to about −0.05 V. Finally, the FIG. 19 graph shows that as the potential difference decreases from about −1.5 V to about −0.05 V the iodine value drops, and particularly as the potential difference decreases from about 0.5 V to about −0.05 V.

Figure 20:
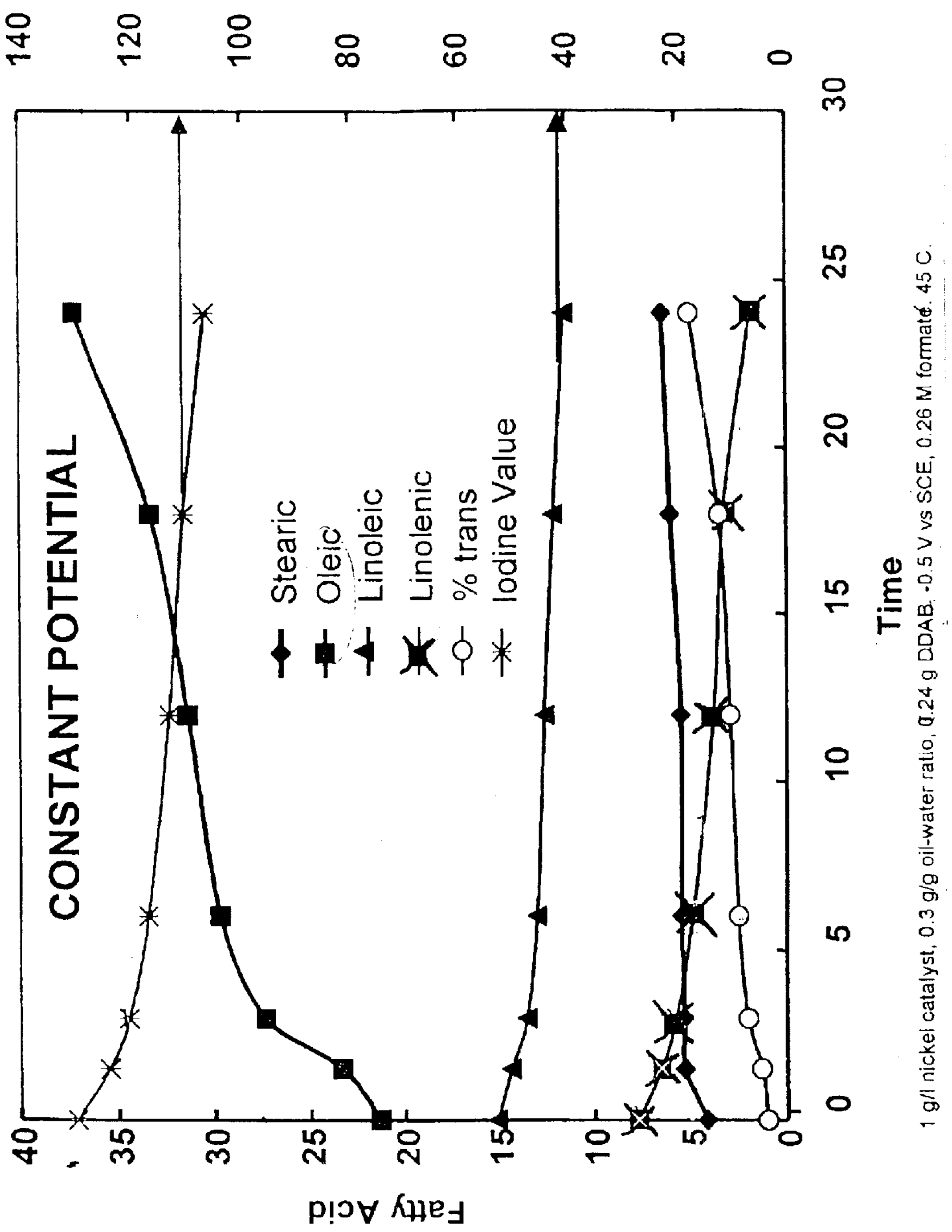
FIG. 20 is a graph of the stearic, oleic, linoleic, and linolenic and trans-fatty acids (left side scale), and the iodine value (right side scale), versus time for a hydrogenation process in accordance with the principles of this invention.

FIG. 20 is a graph of the stearic, oleic, linoleic, and linolenic and trans-fatty acids (left side scale), and the iodine value (right side scale) for a hydrogenation process in accordance with the principles of this invention, at a constant potential. The FIG. 20 graph shows that at a constant potential, the content of the more unsaturated linolenic (18:3) acid and linoleic (18:2) acid decrease over time from about 0 hours to about 25 hours. The FIG. 20 graph also shows that at a constant potential, the content of the relatively more saturated oleic (18:1) acid and the saturated stearic acid (18:0) increase over time from about 0 hours to about 25 hours. The FIG. 20 graph also shows that the trans-fatty acid content increases slightly over time from about 0 to about 25 hours, but does not increase above about 5%. The FIG. 20 graph also shows that the iodine value decreases relatively steadily over time from about 0 hours to about 25 hours.

Figure 21:
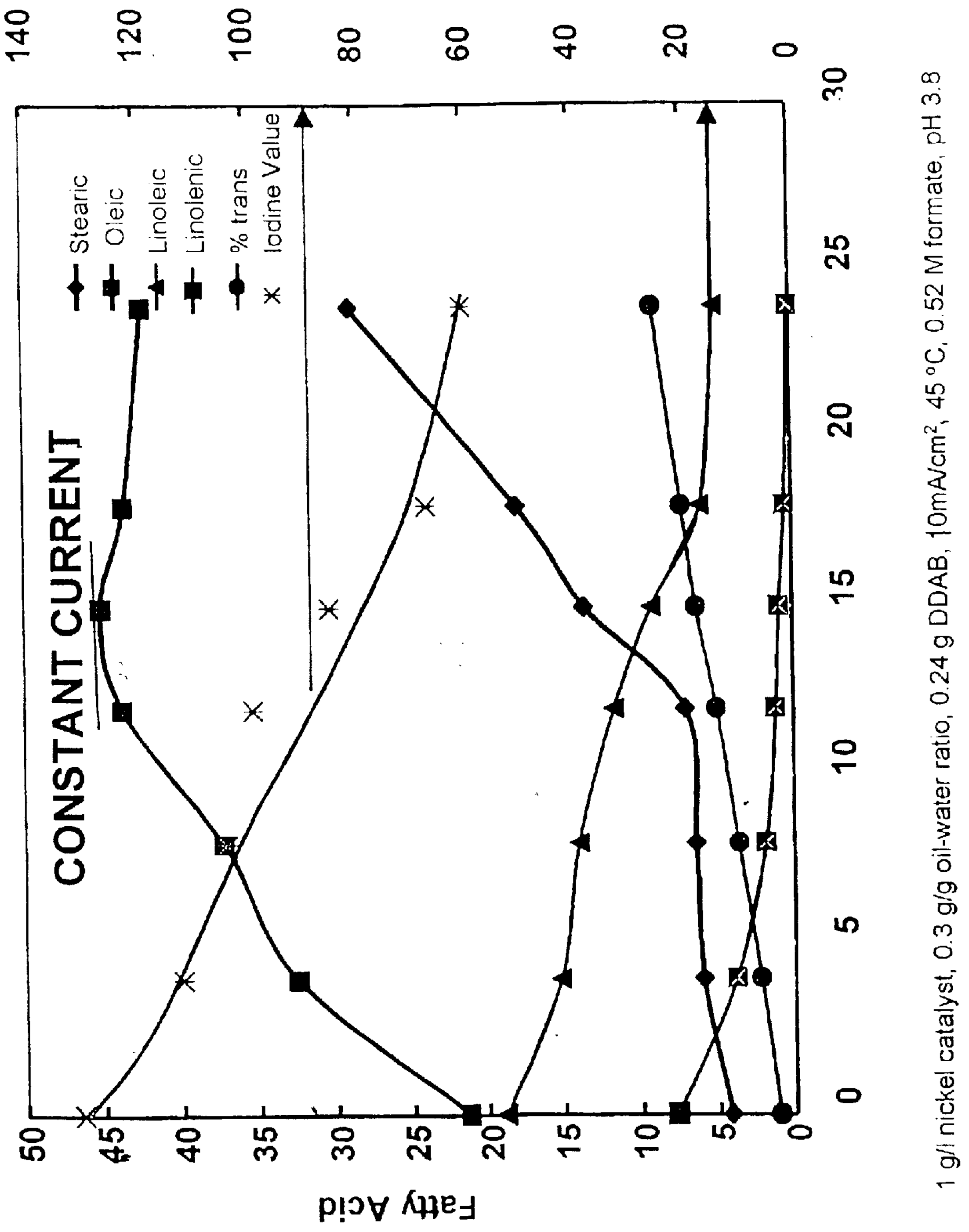
FIG. 21 is a graph of stearic, oleic, linoleic, and linolenic and trans-fatty acid composition (left side scale) and iodine value (right side scale), versus time for a hydrogenation process in accordance with the principles of this invention.

FIG. 21 is a graph of stearic, oleic, linoleic, and linolenic and trans-fatty acid composition (left side scale) and iodine value (right side scale), versus time for a constant current hydrogenation process in accordance with the principles of this invention. The FIG. 21 graph shows that at a constant current, the content of the more unsaturated linolenic (18:3) acid and linoleic (18:2) acid decrease over time from about 0 hours to about 25 hours. The FIG. 21 graph also shows that at constant current, the content of the relative more saturated oleic (18:1) acid increases from about 0 hours to about 15 hours, and thereafter starts to decrease, and that the content of the saturated stearic acid (18:0) increases over time from about 0 hours to about 10 hours, and thereafter increases more sharply. The FIG. 21 graph also shows that at constant current, the trans-fatty acid contents increases slightly over time from about 0 to about 25 hours, but does not increase above about 10%. Finally the FIG. 21 graph shows that the iodine value decreases relatively steadily over time from about 0 hours to about 25 hours.

Figure 22:
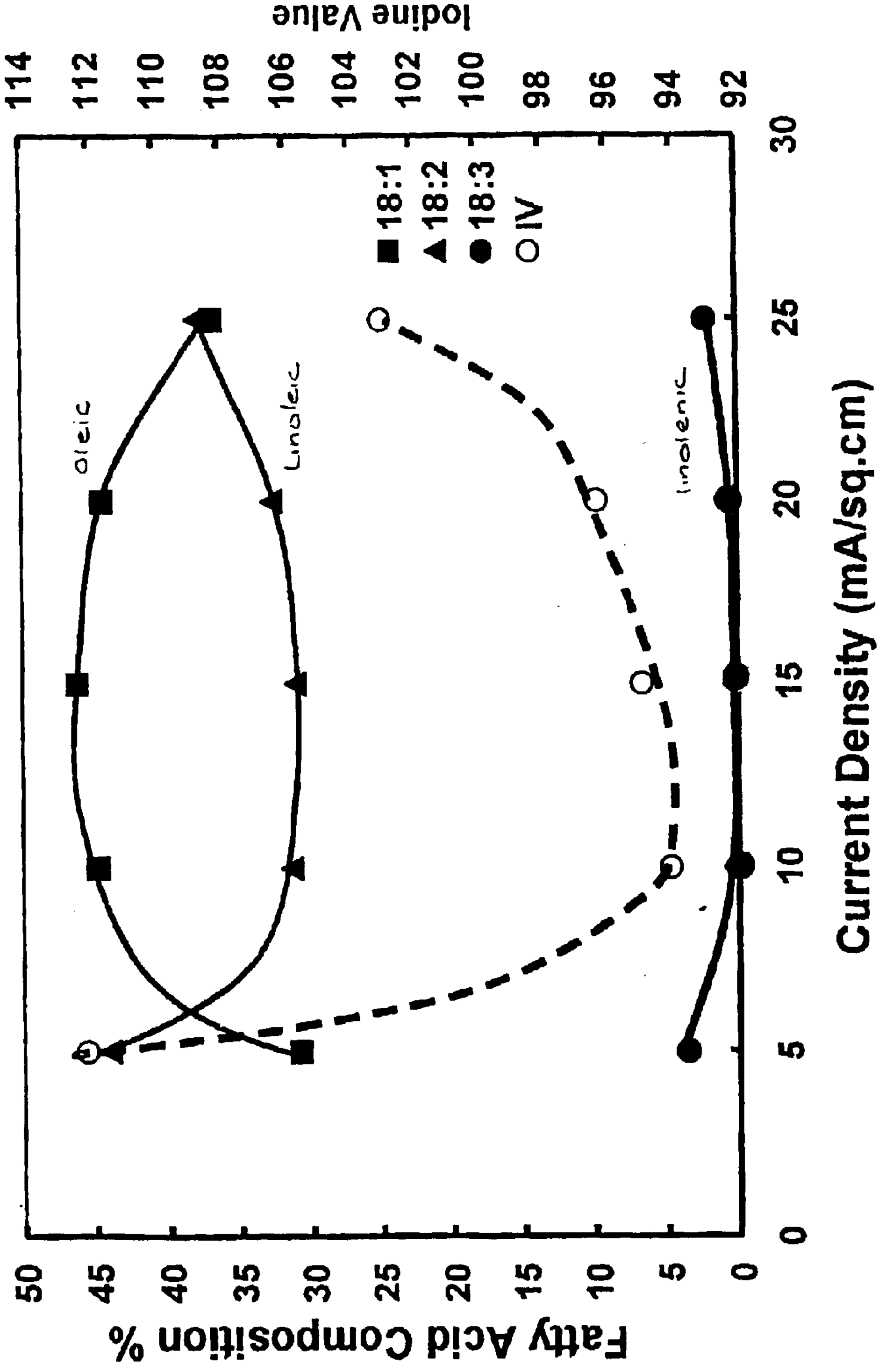
FIG. 22 is a graph of oleic, linoleic, and linolenic acid composition (left side scale) and iodine value (right side scale) versus current density for a hydrogenation process in accordance with the principles of this invention.

FIG. 22 is a graph of oleic, linoleic, and linolenic acid composition (left side scale) and iodine value (right side scale) versus current density for a hydrogenation process of this invention. The FIG. 22 graph shows that as current density increases from about 5 $mA/cm^2$ to about 10 $mA/cm^2$, the content of linolenic (18:3) acid drops, and remains relatively constant for current densities of between about 10 $mA/cm^2$ to about 20 $mA/cm^2$, and increases for current densities from about 20 $mA/cm^2$ to about 25 $mA/cm^2$. Similarly, the FIG. 22 graphs shows that as current density increases from about 5 $mA/cm^2$ to about 10 $mA/cm^2$, the content of linoleic (18:2) acid drops, and remains relatively constant for current densities of between about 10 $mA/cm^2$ to about 20 $mA/cm^2$, and increases for current densities from about 20 $mA/cm^2$ to about 25 $mA/cm^2$. The FIG. 22 graph shows that the content of the relatively more saturated oleic (18:1) acid increases as current density increases from about 5 $mA/cm^2$ to about 10 $mA/cm^2$, and continues to increase at a lower rate up to about 15 $mA/cm^2$, for current densities between about 15 $mA/cm^2$ to about 20 $mA/cm^2$, the oleic acid content starts to decrease slightly, and between 20 $mA/cm^2$ and 25 $mA/cm^2$, the oleic acid content drops more sharply. Finally, the FIG. 22 graph shows that as the current density increases from about 5 $mA/cm^2$ to about 10 $mA/cm^2$, the iodine value decreases sharply, as the current density increases from about 10 $mA/cm^2$ to about 20 $mA/cm^2$ the iodine value increases slightly, and as the current density increases from about 20 $mA/cm^2$ to about 25 $mA/cm^2$, the iodine value increases sharply.

Figure 23:
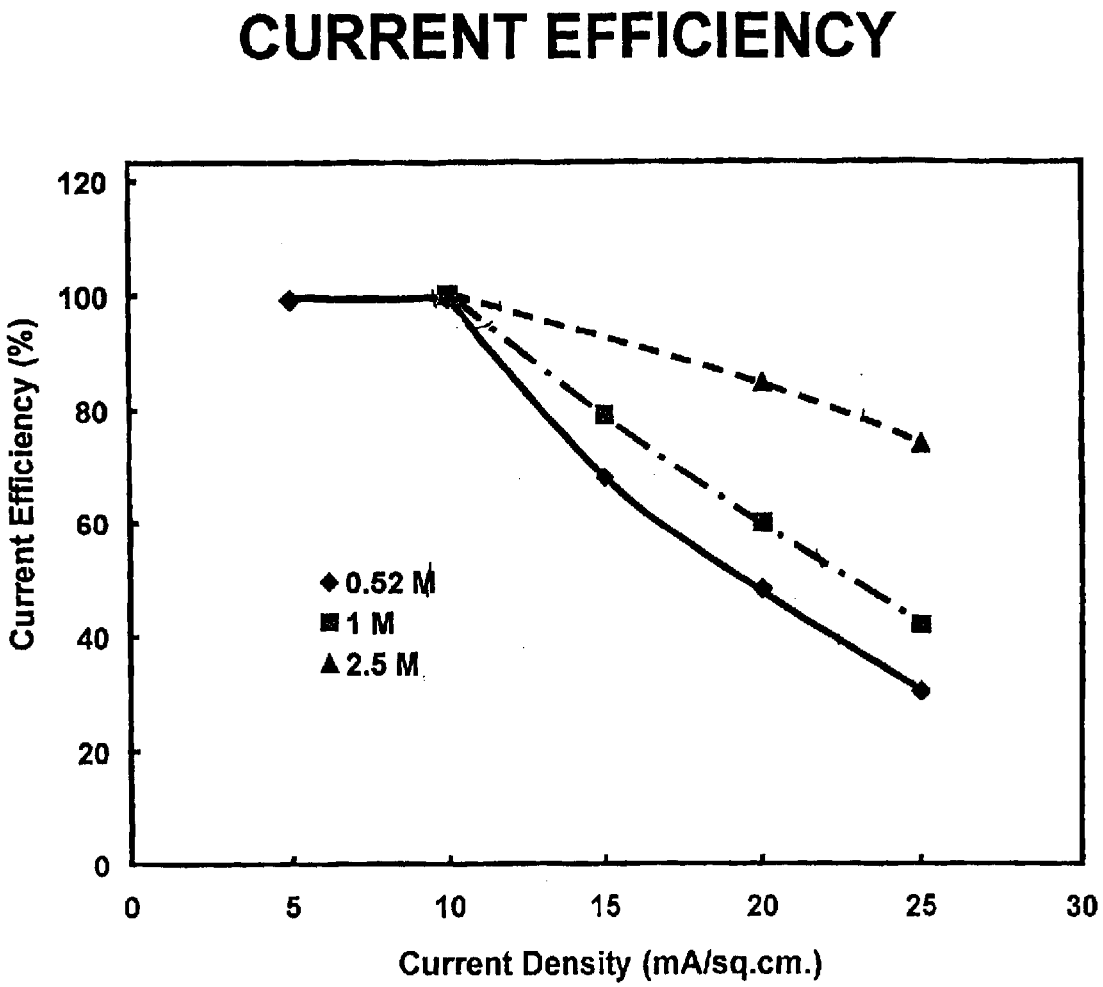
FIG. 23 is a graph of Faradaic Current Efficiency showing current efficiency versus current density for three concentrations of formic acid.

FIG. 23 is a graph of Faradaic Current Efficiency showing current efficiency versus current density for three concentrations of formic acid. It is seen that Faradaic Current Efficiency increases with decreasing current density, achieving nearly 100% at 10 $mA/cm^2$. In addition, Faradaic Current Efficiency also increases as the concentration of formate ion increases.

Figure 24:
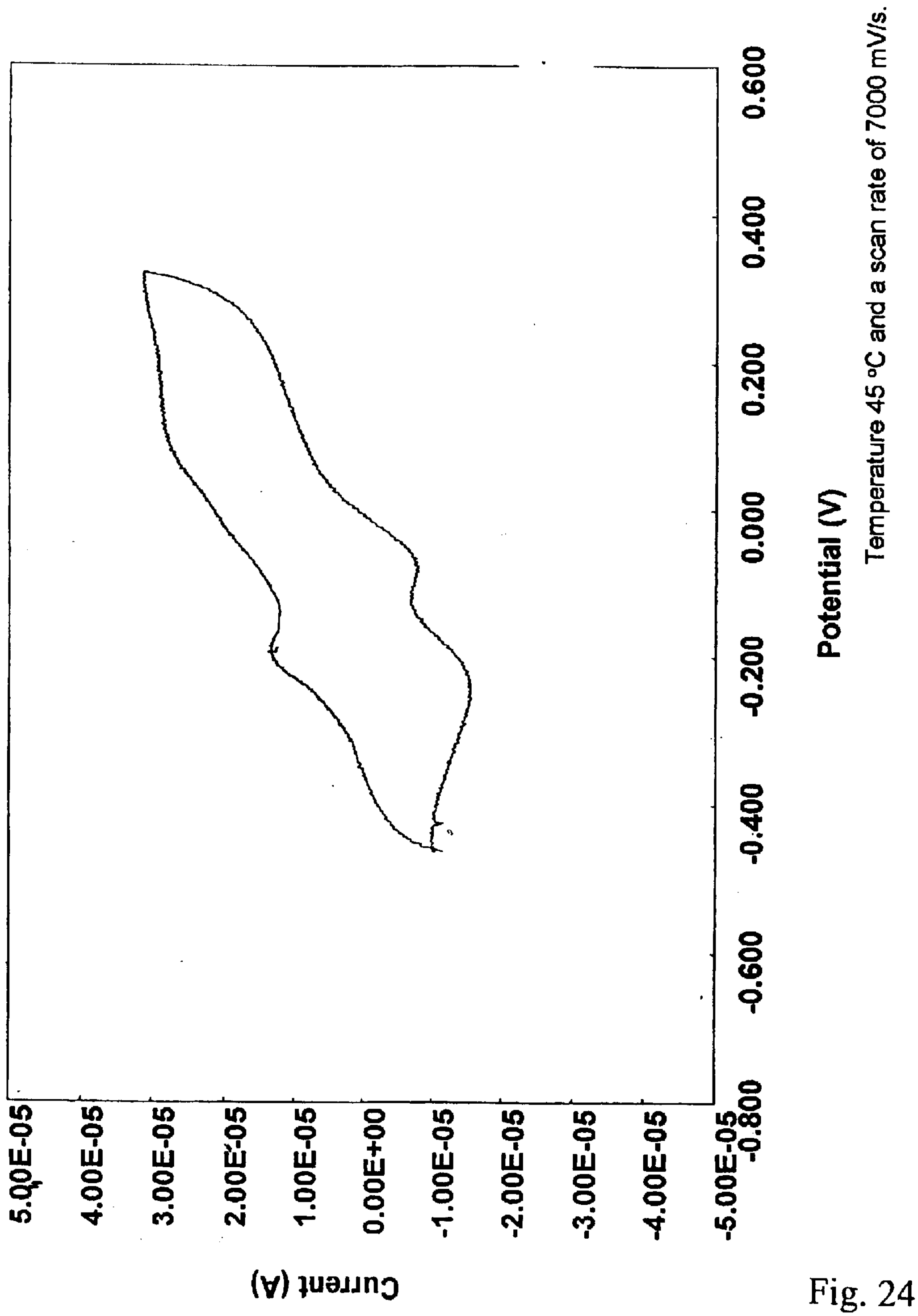
FIG. 24 is a graph of current versus potential for the oxidation/reduction reactions of the formate-bicarbonate couple obtained via cyclic voltammetry technique.

FIG. 24 is a graph of current versus potential that shows that upon increase in the potential from −0.4 V to 0.4 V vs. SCE (reference electrode) two peaks are observed. The first peak is characterized by oxidation of the formate ion to bicarbonate ion, and the second peak refers to oxidation of the bicarbonate to carbonate. When the potential is scanned from 0.4 to −0.4 V vs. SCE, two peaks corresponding to the reduction of carbonate to bicarbonate, and regeneration of formate ion from the bicarbonate ion are observed. The data show that formate ion which is oxidized during hydrogenation of unsaturated oils is capable of being regenerated from its oxidized forms of bicarbonate and carbonate ions as long as the necessary potential or current is maintained.

The trans fatty acid content of oil hydrogenated by the methods in accordance with the principles of this invention is significantly lower than that observed for all other processes including the commercial method of hydrogenation.

Amorphous alloys of nickel produced on carbon and alumina support are significantly less susceptible to dissolution in oil and water as compared to the Raney nickel catalyst used in commercial and other hydrogenation processes. Amorphous catalyst of nickel on carbon and alumina supports is as effective in terms of reaching low trans fatty acid production as is the nickel catalyst used in this invention. Both, amorphous nickel and nickel catalysts are equally viable for reducing unsaturated fatty oils.

What is claimed is:

1. A method of electrochemically hydrogenating an oil, the method comprising reacting unsaturated fatty acids in the oil with hydrogen in the presence of a formate electrocatalyst.

2. The method according to claim 1 wherein the source of the formate electrocatalyst is at least one of formic acid and sodium formate.

3. The method according to claim 1 wherein the hydrogen is generated at the cathode of an electrochemical cell.

4. The method according to claim 1 wherein the formate electrocatalyst participates in the hydrogenation reaction as a mediator providing hydrogen atoms to the fatty acid to become a bicarbonate and being regenerated at the cathode of an electrochemical cell.

5. A method of electrochemically hydrogenating an oil, reacting the unsaturated fatty acids in the oil with hydrogen in the presence of a formate catalyst in an electrochemical cell that generates oxygen at the anode, and regenerates the formate catalyst at the cathode.

6. The method according to claim 5 wherein the reaction is conducted in the presence of a nickel catalyst.

7. The method according to claim 5 wherein the reaction is conducted in the presence of a palladium catalyst.

8. The method according to claim 5 wherein the electrocatalyst concentration is between about 0.5 M and about 1.5 M.

9. The method according to claim 5 wherein the pH of the cell is greater than about 2 and less than about 8.

10. The method according to claim 5 wherein the oil is in the form of an a oil and water emulsion, with the ratio of oil:water is the cell is between about 0.2 and about 0.3.

11. The method according to claim 5 wherein the temperature of the electrochemical cell is less than about 60° C.

12. The method according to claim 5 wherein the reaction is catalyzed, and wherein the catalyst is present in an amount less that 2 grams/liter.

13. A method of electrochemically hydrogenating an oil, the method comprising reacting unsaturated fatty acids in the oil with hydrogen in the presence of a formate electrocatalyst under conditions to mitigate the formation of trans fatty acids.

14. A method of electrochemically hydrogenating an oil, the method comprising reacting unsaturated fatty acids in the oil with hydrogen in the presence of a formate electrocatalyst and an amorphous nickel alloy catalyst.

15. The method according to claim 14 wherein the amorphous nickel alloy is on a carbon support.

16. The method according to claim 14 wherein the amorphous nickel alloy is on a alumina support.

17. A method of hydrogenating an oil containing unsaturated fatty acids, the method comprising reacting an emulsion of oil and water in an electrochemical cell in the presence of a formate catalyst to hydrogenate the unsaturated fatty acids under conditions that inhibit the formation trans-fatty acids to less than about 10% of the oil content.

18. The method according to claim 17 wherein the electrochemical cell is operated such that the formate electrocatalyst as a mediator in the hydrogenation reaction providing hydrogen atoms to the fatty acid to become a bicarbonate and, wherein at least some of the formate electrocatalyst is regenerated at the cathode of an electrochemical cell.

19. The method according to claim 18 wherein the reaction occurs at a temperature of less than about 70° C.

20. The method according to claim 18 wherein the reaction occurs in the presence of a catalyst selected from the group comprising Ni—P/Carbon (NIP—C), Ni—P/powder (NIP—P), and Ni—P/alumina (NIP—A).

* * * * *